US006693227B1

United States Patent
Gittins et al.

(10) Patent No.: US 6,693,227 B1
(45) Date of Patent: Feb. 17, 2004

(54) INDUCIBILE PLANT PROMOTERS

(75) Inventors: John Robert Gittins, Havant (GB);
David John James, Maidstone (GB);
Elizabeth Rachel Hiles, Aylesford (GB)

(73) Assignee: The Minister of Agriculture Fisheries and Food in Her Britannic Majesty's Government of the United Kingdom and Northern Ireland, London (GB)

(*) Notice: Subject to any disclaimer, the term of this patent is extended or adjusted under 35 U.S.C. 154(b) by 0 days.

(21) Appl. No.: 09/415,161

(22) Filed: Oct. 5, 1999

Related U.S. Application Data

(63) Continuation of application No. PCT/GB98/01000, filed on Apr. 3, 1998.

(30) Foreign Application Priority Data

Apr. 9, 1997 (GB) .............................................. 9707193
May 31, 1997 (GB) .............................................. 9711233

(51) Int. Cl.$^7$ .......................... A01H 5/00; C07H 21/04; C12N 5/10; C12N 15/82
(52) U.S. Cl. .................... 800/287; 435/320.1; 435/468; 435/419; 435/6; 536/24.1; 800/315; 800/286; 800/283; 800/279; 800/302
(58) Field of Search .............................. 435/320.1, 468, 435/419, 6; 536/24.1; 800/287, 315, 286, 279, 283, 302

(56) References Cited

U.S. PATENT DOCUMENTS 5,530,190 A   6/1996   Grierson et al. ............ 800/283

FOREIGN PATENT DOCUMENTS

| AU | WO 9413797 | 6/1994 |
| AU | WO 9711166 | 3/1997 |
| GB | WO 9314212 | 7/1993 |
| GB | WO 9321334 | 10/1993 |

OTHER PUBLICATIONS

Yuan, L. and Knauf, V. C., "Modification of plant components." 1997, Current Opinion in Biotechnology, vol. 8, pp. 227–233.*

Montgomery, J. et al., "Identification of an ethylene–responsive region in the promoter of a fruit ripening gene." 1993, Proc. Natl. Acad. Sci. USA, vol. 90, pp. 5939–5943.*

Mainiatis et al., Molecular Cloning, 1992, Cold Spring Harbor Laboratory, pp. 387–389.*

Woo Taek Kim et al. Induction of 1–Aminocyclopropane–1–Carboxylate Synthase mRNA by Auxin in Mung Bean Hypocotyis and Cultured Apple Shoots. Plant Physiol. (1992) 98.465–471.

Gavin S. Ross, et al. Apple β–Galactosidase. Plant Physiol. (1994) 106:521–528.

Houqi Chen, et al. Nucleotide sequence of an apple nuclear gene encoding a light–harvesting chlorophyll a/b binding polypeptide of photosystem 11. Nucleic Acid Research. 18,3:679.

Michael Lay–Yee, et al. A Full–Length cDNA Encoding 1–Aminocyloropane–1–Carboxylate Synthase from Apple. Plant Physiol. (1995) 107:1017–1018

Jyothi Thimmapuram, et al. Isolation of apple genomic clones containing putative β–1,3–glucanase gene(s). Progress in Temperate Fruit Breeding. (1994) 339–342.

* cited by examiner

Primary Examiner—David T. Fox
Assistant Examiner—David H Kruse
(74) Attorney, Agent, or Firm—Dann, Dorfman, Herrell & Skillman, P.C.; Kathleen D. Rigaut

(57) ABSTRACT

The invention relates to a recombinant polynucleotide comprising a promoter sequence being an inducible promoter obtainable from apple. The promoter sequence is preferably activated in response to which agents are specific to ripening fruit and is most preferably the apple β-galactosidase (ABG1) promoter. Vectors form a further part of the invention. Also provided are host plant cells, plus methods of producing transgenic plants and fruit which incorporate antisense RNA capable of down-regulating genes involved in ripening or peptides or proteins improving fungal, insect, bacterial, viral, herbicidal, nematode, or arachnid resistance. Such transgenic plants and fruit have storage and pest-resistance properties superior to non-transgenic varieties.

9 Claims, 22 Drawing Sheets

Fig. 1A

1. ABG EcoRI fragment Forward

```
GATTCTTATTCCACATGTATTACACAAACATAAATTAGGAAGTTCTTCCTCCTCCTAGGAATCCAAATCCTCAAAGGTTTT

CCCTCTCTAAGGAATCCTATTCCCTCATAGCCCTTGCGACGTTTATATATACGGATTCACCATACAAATGAAATACAACAGA

TACAGTATTTTCTACAGACACCCGTATTTCCAAAAATGTGAGAGAGCTTGTTCAAGGCAGCAGAAGTGGCCCCCCCCCCCT

TCCCCTTTGCAGTTTGCACATTTGCAATCTTCATCTTCAAAACCTTATTTAAAGCAGTAGCGGGAGCAACACGTTCCTTGC
                                                                start of cDNA sequence
                                                   CTCAACTCTGCCACTCTCTCTCTG
ACAACCATTGAACCAAACCATAAACTTTCTCCACCCGTGAAATCCAGCAGTACACTTCTCTACTCTGCCACCCCTTNCTG TCTCTTTCCAAAATATCAAAAGCACCAAACAAAGAAA---CCAAATTC-AAATCCCAAAACACAA-TATATATT--TT
TCTCTTTTCCGAATACCCAAANGCACCAAAC_CCAAAGAAACANTTCCAANTCCCAAAACCAAAAAAATAAATATGTATTATTC AAGTTTTTGGTACAAACAAAG-CAAGT-ATATTTATATATAAAGGCCATTGCTTTTGAGCGTTTCAGAAGCAAGGGAAAA
AAGTTTTGGGTACAAACAAANGCAANTTATNTNTATTATTNANGGCCATTGCTTTNGGATTTTCAGAAGCAGGGACAA

1
 M
ATG   SEQ ID NO.8
A--   SEQ ID NO.10
```

1. XhoI deletion-Reverse

```
NAGGGGGGAACANTTAANTTTCAGGTGTTGGTTGNGGATTTTNAGGGANTCAAAAAAGTTGGATCATAATGT

TAGGAAAGGGAACCAGGAATTTTAAAAAGGAGATTTTTTAAAAAGGAGATTNTTCATAATNNNTTTNTTNAGG

TTTGGGGGACAATATTTATAATAATATGGGGGGCAAAAATTAAANGTTAAAATGTAAGATAAANAGNGAATTCAT

AGAAGGCAAACAATTTTAAGATAATNTCCTNAACATTTATAAAAAATATGAANANTCAGTGGGANGTGTCA

TTCCCTTTGTTAGACAAATAATTTCTATATATTTAAATTTATATTATTACTTTTTTGNTATATATAGACC
                                         start of cDNA sequence
----------------------------------------ATCCAAAAACCAAAACCTCAAACTCTCTC

CCTCCAGTCCAACAACATCCAATATCCCANTTCAAACTTGTAATCCAAACTTCAAAACCTCAAACTNTNTN

TCTATTGCTTTCTCTTCCTTTCCACACTTCTCTTTCCTTACAGCTTGTATCCATACACAAGAAAATTAACCAA
TNTATNGCTTTNTNTTCCTTTCCACACTTNTTCTTACAGCTTGTATCCATACACAAGAAAAATTAACCAA
1
```

Fig.2 (Cont).

```
M  R  M  L  S  R  N  A  T  E  N  S  H  G  Q  D  S  Y  E  L  G  W
AATGCGCATGTTATCCAGAGAAACGCTACGTTCAACTCTCACGGCCAAGACTCCTCCTACTTCTTAGGTTGG
AATGCGCATGTTATCCAGAAGAAACGNTACGTTCAANTNTCACGGCCAAGACTCCTCCTACTTCTTAGGTTGG

Q  E  Y  E  K  N  P  Y  H  E  V  H  N  T  N  G  I  I  Q  M  G  L  A
CAAGAGTATGAGAAGAACCCCTACCATGAGGTCCACAACAAACACAACGGGATTATTCAGATGGGTCTAGCAG
CAAGAGTATGAGAAGAACCCCCTACCATGAGGTCCACAACAAACACAACAAACGGGATTATTCAGATGGGTNTAGCAG
                     49

E  N  Q
AAAATCAG----------------------------------------------------------------
AAAATCAGGTAATTAATTATTATAATTTACGAGCTTAATTTTTTATTACTACCATGCATATATGTTACCA
                                                                    50

L  C  E  D
-------------------------------------------------------CTCTGTTTTGAT
TATGTAGTTATATTTAGTATATATAAACTTTGTGCGCGTTTCAATATTTTTTTTTCTAGCTCTGTTTTG-T

L  L
CTTCTC SEQ ID NO.12
CTTCTC SEQ ID NO.13
```

Fig.3.

```
GCATGCATAGACAACTGATATGGAAAAGTCATTTTAAGAATAATATCTTTATTTTGGAACC
TAGGCTGTTTTTTACCACATAAATGATATCAGGGCAATTTCTTTCGACAAAGTCTTTCTTC
AAATGGCACTGTAAGAATCCAGGGGGAGCTAAATTATTACAACAATTAATACTAAAATTT
GGTTTTTTTTTTCGGTAACAAAACTTAGGGGGAGATTGATTATTCTCACTATATCAGTGC
CAAGACATGTCCACAACTTTGAGCCGGAAGGACTTACGCATGACACCTAACTGTCAGCT
ACCATCAGTATGGATTTACGTAGGAATTTACATATCACATAAAAAATGACTACTGACAACA
GGACTCAAACCTTGGGGGGACGGCACACAAAGTAAAGATCTTACCTACTAAGCCAACC
CTCATGGGCTAAATTTTGGTAATTTCATGATTAATGTAAGTAATAGAAACATCAATTATTTC
TTGATATATAAAACAATTTTAAATATTCAATATTCAAATTAGACCAACAAACATTGTTGAGTT
TGTCTCATAAGATTTGGGGATTGATGTATTTGTTAGTCACTCACAAGCTTCATCACCTAG
CATAACGATAATAGTTTGAACCTTGATGGTTAAATGGAGAAAAAATGAGAAGAAAACAAA
ATTTCCATGCAACATCGATTGCACACGTGTCGGACCACGATCGGTAGCTAGCTTCAATG
TCCAGAGAGGGCACTGGAAATTCTTTGTTCTGGAGTCAAAAGTATAACTGCATCACTGC
TTGCAAGCCGTACATTAAATATGTGGCAACTTGATCTTGATACTTTCCGACAAGTATGAC
CAAAAGTAAAGTAATTTATTTTAATCTTTAAAGAATGAATAGTATTGAGCACCGTCCAAGTA
AGGTGATTCTTGTATTTTCCCTGAAGCTTAATTTTACTATTGTCTTGTGACTTTTGTACACA
TATCAATTTAGACTTTTCCGTAAGGGTAAATGGAAAATCAAGCTTAAAGTCATGAAAACCA
ACAAACCTATTTATTGTTTTTCGATTCTTGATAAATTCTCGTATGTTATTGGTTGTATAGGAT
CTTGTGTATATCGTTTCATTACCTGAAAAGTATAAACACATAATTATATATAAGGAAAACTA
ATGAAAATGATTTGAAAACTTTGAGTTTTAACGATAAAGACAAAATAAAGGGTAAAGTGAA
TAGTACAAGGATTGACTTTTTAGTGTAAAAATGTGATTTTTCGTTAAGTGAACAGTACCGG
GAACTTTTCATTAAAGTTCCCGCATGAAACACACTTTTTTTTTTTAAGGTGATAAAGGATTTC
GTTCATAATTAACGAAATGAACTAATACAGAGAGCATGGATAAGAAGTGGCCTTGAAAAA
CCTCGTCCTAAGTAATCCACATAAAAAAAACTTTGAGAGAGAAAAAATAGCAACCCATGC
TAGAAACAGAACACATCACGTTAAAGTATAATCATCAAACACACAACTTATTAGCTAAGAA
AAGATATTGGGTGAATGATGATTAAATGAAAATAAAATAAGAAAAACAGAAATCGGATTG
GATGATTTAAGACAAATAAAAGGAAAAAAATCGATCGATCACCTTATCCTATAACAAAAA
TTGGAATCCTTCATTTTTAGATGTCTAAATATATACATGAAAAGGAAATCCTTATCCATATT
AATATGGTTTGGTAGTGTTTTTATTATTTACAAATTTCTTTTGTTTGGTCCCAAAGGGGAA
CAATTTTTAATAGATTCGTTTACCGGCATGGATAGACCCATGCAAAGCTTTTCTTCAAATA
TCTGATTGACACATCAATTTAGAAATTGAGTAACATCTCTATCAAATGAAAACTTCATATTG
CAAATCACATTTCCTTAATTTTAGCAAACAGAAAAAGGAAATTGAAAGGATAAGCTCAAAT
AATTTCATAAATTGTTAAAACTGAATCAAAAGTTCGTTTGATTGCCTTGATTTCGCGAGAA
AATGCTTACCCTCGTAAAAAAAAGAATCATGTCGTTTAAATAAGTTTGATTTGGACGTTTT
GACGGTTTTTTGTCAACTCTTATAGAAGTTTCATCAAATGTCAATGATAGAATAACATCTTA
GCTAGGATTTCGTGTTCCACATGTATATACAATACATAAGCATAAATTAGAAAGTTCATCT
TTTAAGAATCCAAATCCTCGAAGGTTCTCCATCGAGGAATCCTATTCCATATAGGAAACG
GAATTCCTTATTCCACATGTATTACACAAACATAAATTAGGAAGTTCTTTCTCTCCTAGGA
ATCCAAATCCTCAAAGGTTTTCCCTCTCTAAGGAATCCTATTCCTCATAGCCTTGCGACG
TTTATATACGGATTCACCATACAAATGAAATACAACAGATACAGTATTTTCTACAGACA
CCCGTATTTCCAAAAATGTGAGAGAGCTTGTTCAAGGCAGCAGAAGTGGCCCCCCCCC
CTTCCCTTTGCAGTTTGCACATTTGCAATCTTCATCTTCAAAACCTTATATAAAGCAGTAG
CGGGAGCAACACGTTCCTTGCACAACCATTGAACCAAACCATAAACTTTCTCACCCGTG
AAATCCAGCAGTACACTTCTCTACTCTGCCACCCCCTTTCTGTCTCTTTTCCGAATACCA
AAAGCACCAACCAAAGAAACCAAATCCAAATCCCAAAACCCAAAAAAATAAATATGTATTA
TTCAAGTTTTTGATACAAACAAAAGCAAATATATATATTATAAAGGCCATTGCTTTTGAGAT
TTTCAGAAGCAGGGGACAAATGGGTGTTGGAAGTCAAACAATGTGGAGCATTCTGCTA
CTGCTTTCCTGCATTTTTTCTGCAG                                SEQ ID NO.1
```

```
GAGCTCGTTAAATAAAATATTTGATTTCTAAAAAAAATGGACCCCCTAAATAAAGTATTTG
GATTCTAGATATAATATCTCTTTCTTTTTGTTATTATATTTTCAATATAATTATTAGTTCGGT
GATAGATATTAGTTATTTGGTTTTCAGTGTATGGAGATTAGTTGTTTAATTTGTGTATAATT
ATTCTTCATTTGTTTTTGTTAAATGTAATTTTTTTTTTCAAAAATTTATTTGTAATTGGTATCT
CTGGATTTTACTAACTAGTTTGTGTGTTTTCTTTATAATGCTAAACTGCTAATTGCTTGAA
AACTTTATAGTTGCATGCATATTCTAGTTTTGAAGTAAGGTATGAAACTAGTATTTTAGAT
GCAATGGGTAAGTTGATGATATAAATGAGTCATCTTTTGAAAGTCTTCTTTTTAATTTATC
TGATAATAGTTTGTCACAAGACTCGTTTGGAAGTACTTTTAAAATGACTGAAAGCACTTT
TGGTGAAATTGATTTTGGTTCCAAAAGCGTGCTTTTTGGAAGAAGCATCAGGTATTTGC
TTCTATACTTCTTGTAGAAAGCACTTTAAGTGCTTTTCCATGATGCACTTGAATTTTTATT
GAAGATTGGTTTCAAAAACATTTTCACTAAAAGCGCTTTCAAACATTTTAAAAACACTTCC
AAACGAACCCATAATAGAAGGAAATTTATAGTACCTTTTTTATTAATTCATAAATAATCTAA
TGTTAAATCCTTTGAAAGTATATAGTGTATATAATTTCATGGAATCATAATTAACAGAAGT
ATTGAGATGAATACATTGATGGGAGAATGGGCCTTGCATCAAACTATAAGTTGGGTTAT
TCCCTATATTATTGATTGATTTTATGGTGGATCCTCAAATTTGTCATGATATCATAGCAAG
TTGACCCATGTGTAATAGTGAACAACACCATGCAACAATCCTCGCAACCAGTAGTGGC
CCTTGTAGCGAGGCAATAACCCTTGCAGCCGGTAGCAGTGTGCGGCAGTCAATGCC
ATGGCAGTGCAGCACGAAGAAGCAGCCATAACAGTGCAACACGTAGAAAGCAGTGC
AGCAAGGCAGCAGCGGTGCAACAACAAGCAATGCAGTGTACAATAGTGGCAAAAATG
CAACTGGCAATGCAAACATTAGCGAGTGAGTCGACAAGCAATGCGAACATTAACGTGA
CATAAGATGGATTTCGGTCATCCAAGGTTATTTAGGCCATCTCCAACCGAAGGAAGCA
AGAGGGCTTGTTTTAGCCCTTTGGCCCTCCAAGAATATAATATTTTAATGAATAGTGCAA
GGCTATATTTCTTACCATATCCAACCAAGGGGCCAAAGAACCATAGGCCAAACATAGC
CCTGTGACAAAAAATCATCTCCAACCGAGGTCCAAAGAGTCATAGGGCCAAACATAAT
TTATTATTTTAATTGAATTACTATGGTTACTTAAATTAAATTACCTCAATAATTTTATGTTAT
GGATTGTCAATAATTTTCATGTTGTTAAATGTTTTAAAAAATGTTGTTTAAATTTCATATTGT
TAATTTTTTTTTATGTTGTTTAATGTTACTTAATGTTATTTAATGTTGTTTAATATTGTTTAAT
GTTGTTTCATGTTACTTAATGTCACTTAATGTTGTTTAATGACTTAGGAAGTTATAGGAAA
AAAATAGAATTTTTAATTTTTTTTTTAATTTTGTAAAATAAAAAAATTAAATATGATGTCAACAT
GTGGCTTGGCCCAAGGCTGGCTTGTTGGCGAGGTTGGGCCAACCAGTTGGCCCTTT
GGCCCTTTTTTGTCCAATGGGGCCCACAAGCCTTTTGGCCTAGCCCTCGGTTGGAGA
CAGTTTTCGGTCTATTTTCGGCCCTCTAGCCCTCTGGACTATTTGGTTGGAGATGGCTT
TAGACCCCAAAAACTGCGTTTTAGAAAATTTACAAACTTTTCATTTTTGTCCGATCCACTT
TCATTACCCTCCCTAGAGCTTCCCTACATTCGCAGAGTAGTTTTGAGTCATTACACTTTA
TAATTCACCACATTCCCGAAGGAAGAACTAAGTCTAATAAAGCTTTATGGAGCCAAATA
GGTAAAGTGTGTGCATCTCTGCCAAAGGAAAATAGAAGGCTTCAAATCACAAGTCTAA
AAGAAGAGGAGAGGCTTCAAATTAAATTACAAGTCCGTCTCATAGGGTCCTCATATGC
CTATTCATTCATTTCATATTAACGGTGGTAGCCTAAATAAGCACGAAAGCGTTCACTTTG
AGAGGCTTTAAACCATAAGTTTGTGAACCATGTTTCATAGCTCACACTTGTGTTCTTCAT
CAAGTTCATGGAGAATTACCAAGCACAACAAATACATGTGTTGGTTCATCCACATTAAA
GTCGAAGATTGCCCGCCACATGAAACTCCTGGTGGTCCCATTCATTCAAGATCAAACC
TCGACGACCCCTAAAGAAATTATAAGTCTAATTCAAGACCAAGAGTACACCACCCTTGA
ATAAAATTCGCTCTAGAGGAATGAAGTAAATCCAAACCTTTGGAGGAAACCAGAAAGCT
CTTTGCCCAAAGAAAACATTATAATTCTTCATCAAGCTTGTGGAGATTCAACAAGCACAA
AAAAAAAAAAAAAAAAAAAAAAAAACACATACCGATTCGTCCACCATCACGTGAAACTCT
```

Fig.5 B

```
TCATGGTCCCGTTTCATTCAAGACAAGCCTCGATGGCCCTTGAAGAAACTTTCAGCCC
AATTATAGATCAAGCCTCAATGGTCTTGCATCGACATCTATGTTGAGAGACTTCAAAGC
ATACTGATCAAAATACATTCACTATGTGGAGGGACTTCAAAACGCACATTCTACACGTG
ACAAGCACATATATACACCATGCCTTGAAATGGGGTCATTCGTAGACATCAAAATTTTA
GTGAAGTAAATGTTTACCAACACAATAAAATCTTGACGTGCTAGGGCTTACTTGGCATG
CACCATGTGTCTCACAAATCGTACAAATAGCATGTAGCTTATCAAAACTAGACGAGTCA
TCAAGAGTGACACGTGTCAACATTTGGCAAAAATTAATTAAGGATTTATCCTTATTAATTC
TTTGATTAATTTAACTTAAATCAAATAAATTAATTGATTTAAATTTAAAATGTGATTGATTAA
TTGATGGAGTCAAATCACGAACCAAGCTTCAAATCAAGTTCTGGTTCTTTCATCGATGA
ATAAAATCCACAATCAAGGCCAAATCCAACTGTAGGCAAGACTAGGAGAGCCTATAAA
TACGAGGCTCCAAGACAAAGAAATGGGTCAGAAATTCATCAAAACACCTAGACTCTCA
AACTCCCAAACACTCAGAAGATACAGAAAAATCTCTGCATTCTTTGTCATACTTGTGAAG
AACCACCAAGCACCTTTACACATGCCGGTTCCTCCATCGCCATTAGCCAAAACCCTGA
GGCATTTGTTTATTCGAGATCAAGTCATCACGATTTTCGGATCAACAACACACTTTTT
TTCACCCAGAAGATCGAATCAGAGGATTAAAAATTGTAGCAGAGATTGTAACCCTAAAT
TCATTAATACCAATTATTACTTTGTATACGTATTCTTGGGTTATTTATTGCAAGAATTTCGT
GTTTACAACTCTTTTTCTAGCACTTCCATCGACTTATAAGTAATTTAGGCTATTCTTATATT
ACCAATTAATTTTTAGTGGAATCTCAACTTTTTTAAAATTATTTATCTCATGGAAAATCCAA
ATTCTCCTCTAAATGAACGGTTAACAAAAAGGAAACTTTAACGCAAAACTCTCGGTACT
GTTCACTTTAATGAAAAATCATATTTTTACATTAAAAAGTCAATCTTGTTACTATTCACTTTA
CCCTTTATTTTATCCTTATCGTTAAAATTCAAAGTTTTCAAACCCTTTTCATTAGTTTTCCTT
AACAAAAATGGTTTTATTATAACAAATGATTCTAGTGTTTTCCTTGTTTTGTATACCTAATT
CTAAAGGGGATAGAGTGATGATGTTAAATGAAGAAAAAAGAGAGATGCCATTTTTGTT
CGTACCGGATTTTCGAGGTTGACTCAAATCAAAACATTGTTTGGTAATTGGAGTAATGA
ACTGAGCAGACATAAAAACCTGTGCGAACTTAAAGGTTAAAAAAAAGGTTAAAAAAAAA
AAACTTAAACGAAAAAATCTCAGTATTGTTTATTTTAACAAAAAATCACACTTTTACATTAA
AAAGTCAATCCTGTTATTATTTATTTTACCCTTTATTTTGTTTAAAACTCAAAGTTTTTAAGT
ATTTTTCATTAATTTTCCTTAAAAAAAATAGAAAGTGAGAAAAATGCCCGACAAAATTAGT
TGTGGCTACTAGAGTCAAGAAGCATATGGACCAGGGTGGGTCGCTCTTGGCATTTTCT
ATGATACTTGTTGTCGGTAAGGTTTTGTAAACAAAACTAGACCCGAGTATTAATTCTTGT
TTCTTTGTTTTTTTTTCAATTACAAGCCGATTAATGCTTCTATGTACACTTATAATCCCCAC
GCAAGTTTGTAGGTTATGCCAGGTAATGGTGAACGCCCTACCCACTTCCCAGTCCAAG
CAAATAGTGAGAAAATAAATTAATGGATGATACTAGGAAAATTAAATTTGGAGATAAAAT
TTGCAAATTATATAATATGTCACCTATACGAATTAACACATTTATCAATATTTAAATAATAA
ATCAATCATCAACTACCATATAATTTAGTTTCCAAAATTTTATTTACAAATTTAGTCTTTAGT
ATTACCCTCAATTAATTATTTAATGTTGATTAGTAAACACTAAAACTTCATTGCTTTGGGAT
TTGGGAGTGTCTGAAGGTCCTTCATGATCAATGTCTTTAGATGGTGGAGCAAAAGCGC
GTACAATTAATTATCATGTTGTTTTTGGATTTTTATTGAATCAAAATACTTGGATCATAATG
TTAAGAAAAGAACCAGAGAAATCTAAAGAGACTTTCTTAAAAATGAGATTCTTCATAATT
TATTTATCATGTTTTTGGTACAATATTTATAATATCGGGGCAAAAATTAATGTTAAAATGTA
AGATAACAGAGAATTCATAGAAAGCACAATTTTAAGATAATCTCCTTAACATTTATAAAAA
ATATGACTACTCAGTGTGACGTGTCATTCCTTTGTTAGACAAATAATTTCTATATATTTAA
ATTTATATTATTACTTTTTTGCTATATATAGACCCCTCCAGTCCAACAACATCCAATATCC
CACTTCAAACTTGTAATCCAAAACCAAAACCTCAAACTCTCTCTCTATTGCTTTCTCTTCC
TTTCCACACTTCTTTCTTACAGCTTGTATCCATACCCGGG         SEQ ID NO.2
```

Fig. 6A

AASP ACC Synthase

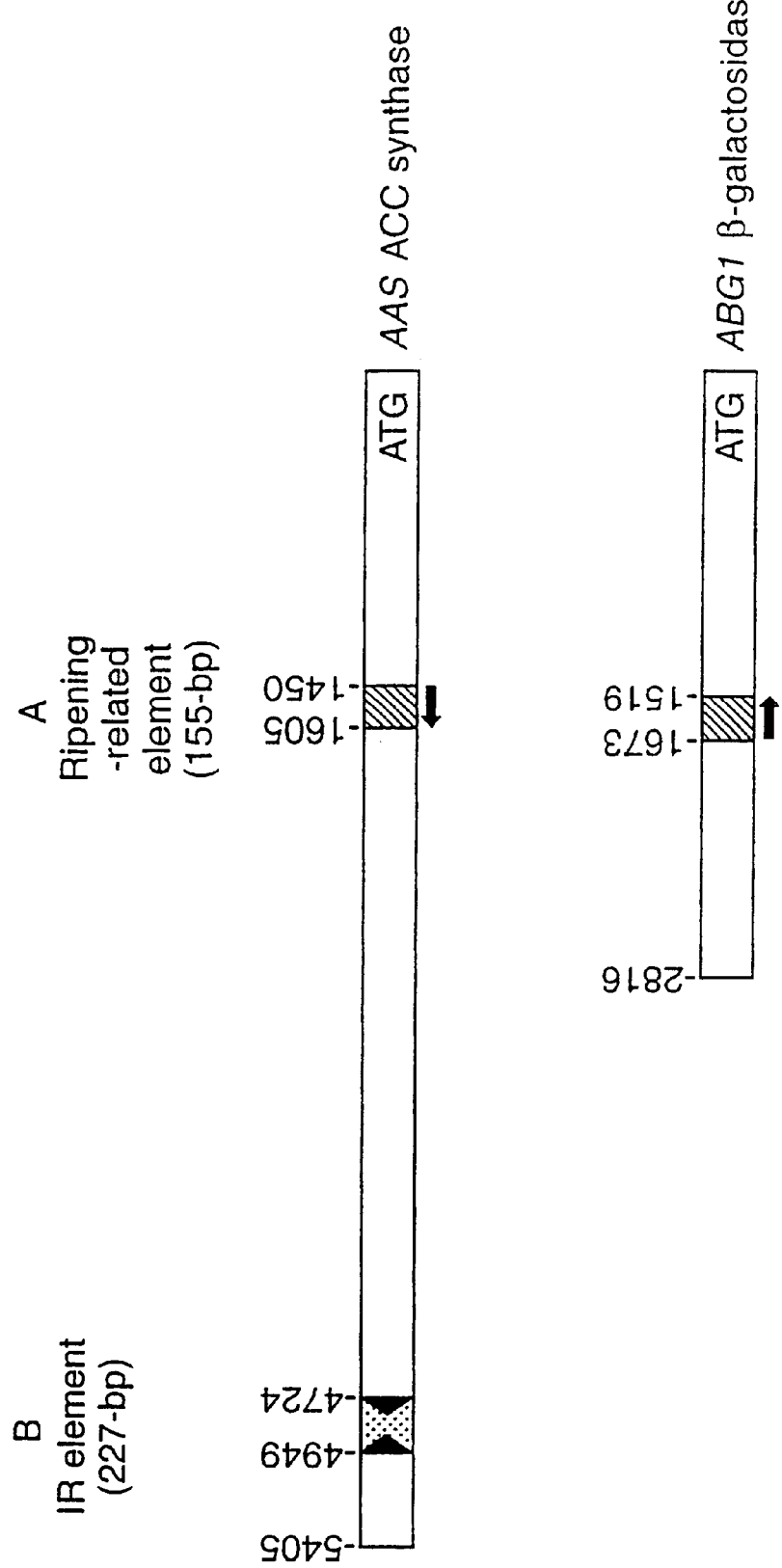

Fig. 8A

Alignment of ripening-related elements found in the *ABG1* and *AAS* promoters

```
1   GAAACTTTACGCAAACTCTGTACTGTTCATCTTTAA  AASP fruitseq
1   GGAACTTAATGAAAAGTTCCCGTACTGTGTTCACTT-AA  ABG1P fruitseq 41  TGAAAATCATATTTTACATTAAAAGTCAATCTTGTTA  AASP fruitseq
40  CGAAAATCACTTTTTACACTAAAAAAGTTAATCTTGTA  ABG1P fruitseq 81  CTATTCACTTTACCTTTATTTATCCTTTAAAAT  AASP fruitseq
80  CTATTCACTTTACCCTTATTTGTGTTATTGTTAAAAC  ABG1P fruitseq 121 TCAAAGTTTTCAAACCCTTTCATTAGTTTTCCTTA  SEQ ID NO.3
120 TCAAAGTTTTCAAATTGATTAGTTTTCCTTA  SEQ ID NO.4
```

Fig. 8B

Alignment of the inverted repeat (IR) element of the *AAS* promoter with that found in the apple Kn-1 knotted gene homologue promoter

```
  1 TTCGTTTGGAAGTGTTTTTGTTTGAAAGCGCTTTT  AASP IRE
  1 CTCGTTTTGAAATTGTTTTTAAATAACTGAAAACATTTTT  KN-1P IRE

41 AGTGAAATGTTTTTGAACCTAATCCTTCAAATATTCA  AASP IRE
 41 GAT-AAAATGTTTTTAGAATCAATTTTAGTAGAAATAGA  KN-1P IRE

81 AGTGCATGGAAGCAAAGCACTTAAAGTGCTTCTAGAAGA  AASP IRE
 80 TGGAATATTGAAAAAGCACTTCAATGCTTCTAGA  KN-1P IRE

121 AGTATAGCAAATACCTGATGCTTCTTCCAAAAACAC  AASP IRE
120 GCAC-GTGTTTCTTGCAGAAAGACC-----AG-GT  KN-1P IRE

161 GCTTTGGAACCAAAATCAATTCACCAAAAGTGCTTWCA  AASP IRE
152 GCTTTGAAATTCAAAAATATTTAAA-TGCATTTTCA  KN-1P IRE

201 GTCATTTTAAAGTACTTCCAAACGAG    SEQ ID NO.5
191 GTCATTTTAAACTACCTTCCAAAATGAG  SEQ ID NO.6
```

INDUCIBILE PLANT PROMOTERS

CROSS-REFERENCES TO RELATED APPLICATIONS

The present application is a continuation of PCT/GB98/01000 filed Apr. 3, 1998, which in turn claims priority to U.K. Patent Application No. 9707193.0, filed Apr. 9, 1997, and to UK Patent Application No. 9711233.8, filed May 31, 1997, all of which are incorporated by reference in their entirety.

TECHNICAL FIELD

The present invention relates to polynucleotides which may be useful in recombinant plant DNA technology or analysis, in particular to tissue- or ripening-specific promoter DNA, and products and methods employing such DNA.

BACKGROUND ART

It is desirable to be able to specifically express (or inhibit the expression of) genes in plants, for instance in particular tissues, or at a particular developmental stage. This may allow particular biosynthetic enzymes to be produced only in the fruit of a plant, and not in other tissues wherein it may have undesirable effects. Likewise it may be desirable to have particular protective proteins (e.g. anti-fungal, pesticidal) expressed only during a particular vulnerable developmental stage e.g. early or late ripening.

This type of specific expression can be achieved by using inducible promoters which are 'switched on' in the presence of environmental signals present only in restricted tissues of the plant, or only at particular times. Such promoters have already been made available for tomatoes. Thus WO93/07257 (SPI Inc.) relates, inter alia, to gene-fusions capable of conferring tissue-specific or developmentally regulated gene constructs. These constructs apparently allow particular genes to be expressed during the formation and ripening of fruit. The coding region of clone λUC82-3.3 in WO93/07257, which was derived from tomato, has homology to a bacterial histidine decarboxylase (HDC). Similarly WO94/13797 (CSIRO) relates, inter alia, to inducible soft-fruit promoter DNA derived from alcohol dehydrogenase (ADH) in tomatoes. ADH apparently has a role in ripening in that it metabolises alcohols and aldehydes involved in flavour. The ADH promoter is apparently sensitive to and therefore inducible by high levels of $O_2$.

It is clear from the foregoing that the disclosure of novel inducible promoters, particularly those active in plants other than tomato plants, would provide a useful contribution to the art.

The applicants have now isolated inducible promoters from apple, elements of which show useful properties and which may be useful in particular in the isolation of other ripening specific promoters or transcription factors, or in the genome mapping studies.

DISCLOSURE OF THE INVENTION

In a first aspect of the present invention there is disclosed a recombinant polynucleotide comprising a promoter sequence being: (a) an inducible promoter obtainable from apple, or (b) a functional portion therof, or (c) a functional derivative or homolog promoter being at least 70% homologous to either.

As used herein, "promoter" refers to a non-coding region of DNA involved in binding of RNA polymerase and other factors that initiate or modulate transcription whereby an RNA transcript is produced. Promoters, depending upon the nature of the regulation, may be constitutive or inducible. A constitutive promoter is always turned on. An inducible promoter requires specific signals in order for it to be turned on or off. These may be particular signals for example chemical signals, which are applied to a cell under certain conditions or as a result of a deliberate application. In the context of the present application, the term "inducible" is intended to include particularly promoters which are tissue-specific in that they are effective only in certain plant tissues either with or without externally applied inducing agents, or ripening specific promoters which switched on within some or all plant cells as a result of ripening, for example in response to ethylene produced during the ripening process.

Examples of promoters of the invention include a ABG1 β-galactosidase promoter whose sequence is included within the sequence shown in FIG. 3 hereinafter (SEQ ID NO 1); and the ACC synthase promoter whose sequence is comprised within the sequence shown in FIG. 5 (SEQ ID NO 2) hereinafter.

Thus, the invention provides a promoter comprising at least a functional portion of the Sequence shown in FIG. 3 or FIG. 5.

As well as authentic promoters obtainable from apple, the invention also embraces functional portions thereof.

The term "functional" is used herein to describe moieties which have the activity of a promoter as defined above, when present in apple cells.

Also embraced by present invention are functional derivative promoters being at least 70% homologous to the above.

By "derivative" is meant a sequence may be obtained by introducing changes into the full-length or part length sequence, for example substitutions, insertions, and/or deletions. This may be achieved by any appropriate technique, including restriction of the sequence with an endonuclease followed by the insertion of a selected base sequence (using linkers if required) and ligation. Also possible is PCR-mediated mutagenesis using mutant primers. Such changes may be introduced e.g. to remove or incorporate restriction sites into the sequence.

Also embraced by the present invention are functional "homologs" of authentic promoters obtained from apple which hybridise thereto and are at least 70% homologous to either the full-length or part length sequences and in particular to SEQ ID NOS 1 and 2 identified herein.

Such homologs may conveniently be identified and isolated by those skilled in the art from a test sample as follows:

The test sample is contacted with the apple promoter under suitable hybridisation conditions, and any test DNA (e.g. an apple genomic library) which hybridises thereto is identified.

Such screening is initially carried out under low-stringency conditions, which comprise a temperature of about 37° C. or less, a formamide concentration of less than about 50%; and a moderate to low salt (e.g. Standard Saline Citrate ('SSC')=0.15 M sodium chloride; 0.15 M sodium citrate; pH 7) concentration. Alternatively, a temperature of about 50° C. or less and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of similarity with the probe sequence, without requiring perfect homology for the identification of a stable hybrid. The phrase 'substantial similarity' refers to sequences which share at least 50% overall sequence identity. Preferably, hybridisation conditions will be selected which allow the identification of sequences having at least 70k sequence identity with the probe, while discriminating against sequences which have a lower level of sequence identity with respect to the probe.

After low stringency hybridization has been used to identify one or more homologs having a substantial degree of similarity with the probe sequence, this subset is then subjected to high stringency hybridization, so as to identify those clones having a particularly high level of homology with respect to the probe sequences. High stringency conditions comprise a temperature of about 42C or less, a formamide concentration of less than about 20%, and a low salt (SSC) concentration. Alternatively they may comprise a temperature of about 65C or less, and a low salt (SSPE) concentration. Preferred conditions for such screening comprise a temperature of about 42C, a formamide concentration of about 20%, and a salt concentration of about 2×SSC, or a temperature of about 65C, and a salt concentration of about 0.2 SSPE.

Thus, according to the present invention the derivative sequence or homolog is at least 70% identical to the sequence of the full or part-length promoters. Typically there is 80% or more, 90% or more 95% or more or 98% or more identity between the derivative or homolog and the authentic sequences. There may be up to five, for example up to ten or up to twenty nucleotide deletions, insertions and/or substitutions made to the full-length or part length sequences.

Whether a part-length or modified or homologous sequence is capable of acting as a promoter (is "functional") may be readily ascertained in the light of the present disclosure by those skilled in the art. Briefly, the candidate sequence is provided in a vector upstream of a protein coding sequence at a position in which it is believed to be operatively linked to that coding sequence. A suitable host cell, preferably an apple cell, is transformed with the resulting vector. The presence or absence of the protein coded by the sequence is determined.

Preferably the polynucleotide of the first aspect comprises a promoter sequence which is activated in response to tissue specific agents i.e. is turned on or off as a function of the tissue in which it is present. More preferably the agents are specific to fruit, and most preferably specific to ripening is fruit (i.e. the promoter is a developmentally regulated promoter which is turned on or off as a function of development).

Two particular examples of promoter sequences of the invention are the Apple β-Galactosidase (ABG1) promoter, or the 1-AminoCyclopropane-1-Carboxylate synthase (ACC Synthase) promoter. Isolated, non-recombinant, polynucleotides encoding these promoters, or functional portions or dervatives or homologs thereof form a further part of the present invention. The sequences of these promoters are included within the sequences given hereinafter in FIGS. 3 and 5 respectively and recombinantly produced or synthetic promoters comprising or derived from these sequences also fall within the ambit of the invention.

Computer-assisted examination of the DNA sequences of the ABG1 (2879-bp) and the AAS ACC synthase (5391-bp) promoter containing fragments of FIGS. 3 and 5 has shown the presence of some interesting sequence motifs as illustrated in FIGS. 7 and 8 below (SEQ ID NOS 3 and 4 and 5 and 6 respectively). These motifs form preferred examples of portions of the ABG1 and AAS ACC synthase promoters.

A: At approximately the same location (1.5–1.6-kbp) upstream from the start codon of these two ripening-related genes there is a highly conserved sequence of 155-bp. The orientation of the sequence is opposite in the two promoters (SEQ ID NOS 3 and 4). These two sequences are 90% similar and contain an unusual repeat element (GAAAAATCACATTTTTACACTAAAAAG-SEQ ID NO 7) or a derivative thereof, which has dyad symmetry about the central T residue. This unit is found in the ACC synthase promoter sequence (FIG. 8) and is varied only by two conservative (T→C) substitutions in the ABG1 sequence. This is believed to be the binding site for a dimeric transcription factor, and considering the extent of conservation of the DNA sequence encompassing this motif, it may be involved in the regulation of transcription during fruit ripening.

This 155 bp DNA sequence could be used as a probe fragment to isolate other ripening-specific promoters by library screening, for example as described above.

Furthermore, as it is likely to be important in ripening-specific gene expression, the sequence could be used as a component of a minimal promoter. Removal of extraneous non-functional sequences is desirable to satisfy regulatory considerations and would reduce the size of promoters considerably, making them more versatile.

Thus in a preferred embodiment, the invention provides a inducible promoter which comprises SEQ ID NO 3 or SEQ ID NO 4 or a functional portion thereof, or a functional derivative or homolog promoter being at least 70!k homologous to either. Preferably, the promoter will comprise SEQ ID NO 3 of SEQ ID NO 4.

These sequences could be used in strategies to isolate transcription factors involved in ripening-specific gene expression. They could be coupled to magnetic beads to affinity purify proteinaceaous factors from extracts of fruit cell nuclei or could be radiolabelled and used to screen a fruit cDNA expression library. Such methods form a further aspect of the invention.

B: Another notable sequence occurs approximately 4.7-kbp upstream of the start codon in the ACC synthase promoter (FIG. 7). This sequence (SEQ ID NO 5 in FIG. 8) of 227-bp has Inverted repeat (IR) elements at its termini. The only significant similarity identified is with a sequence (217-bp) seen in the promoter of an apple kn1-like knotted gene homologue [Watillon, B. (1996), *M.domestica* partial gene for kn1-like protein. GB accession Z71981- SEQ ID NO 6]. The homology is 61% overall, but considerably higher at the termini.

A PCR fragment encompassing the apple kn1-like IR element has been used to probe a Southern blot of genomic DNA. This showed that there are multiple copies of the element in the apple genome and appears to confirm that the sequences represent transposable inverted repeat elements. The identification of such elements has never before been reported in apple.

These elements share some features with the Stowaway class of IR elements [Bureau, T. E. and Wessler, S. R. (1994) Stowaway: A new family of inverted repeat elements associated with the genes of both monocotyledonous and dicotyledonous plants. The Plant Cell 6: 907–916]. Stowaway and similar plant IR elements may represent transposable elements, their remnants after transposition or solo terminal repeats from a larger element.

The apple IR element identified is similar in size to Stowaway elements found in dicotyledonous plants (248 bp+/−24 bp) and is also AT rich. It differs in the target site for insertion (TA in Stowaway) and the nature of the conserved terminal repeat region. It therefore represents a new class of element which has not been reported previously.

The inverted repeat element may be of use in genome mapping in rosaceous species. Depending on how widespread it is and in what copy numbers it is found, it may be used in a similar way to microsatellites. Such methods form yet a further aspect of the invention.

In a further aspect of the invention there is provided a replication vector comprising a polynucleotide as described above and further comprising a replication element which permits replication of the vector in a suitable host cell.

"Vector" is defined to include, inter alia, any plasmid DNA, lysogenic phage DNA and/or transposon DNA, in double or single stranded linear or circular form which may or may not be self transmissible or mobilizable and which can transform prokaryotic or eukaryotic host either by integration into the cellular genome or exist extrachromosomally (e.g. autonomous replicating plasmid with an origin of replication). Introduced by any method e.g. conjugation, mobilisation, transformation, transfection, transduction or electroporation. The term explicitly includes shuttle vectors by which is meant a DNA vehicle capable, naturally or by design, of replication in both bacterial and plant cells.

In yet a further aspect of the invention there is provided an expression vector comprising a polynucleotide as described above. Preferably the vector further comprises a heterologous gene operatively linked to said promoter sequence.

As used herein, the terms "operatively linked" denotes the linkage of a promoter or a non-coding gene regulatory sequence to an RNA-encoding DNA sequence, and especially to the ability of the regulatory sequence or promoter to induce production of RNA transcripts corresponding to the DNA-encoding sequence when the promoter or regulatory sequence is recognised by a suitable polymerase.

Preferably the heterologous gene encodes any of: (a) antisense RNA capable of down-regulating genes involved in ripening; (b) a peptide or protein improving fungal, insect, bacterial, viral, herbicidal, nematode, or arachnid resistance; (c) a detectable or selectable marker protein. Examples of some of such heterologous genes are known to those skilled in the art (see e.g. WO93/07257, WO94/13797). Ripening specific genes include those involved in ethylene biosynthesis or cell wall degradation. Proteins involved in fungal degradation include β-1,3-glucanases and chitinases. Marker proteins include β-glucuronidase (GUS).

Preferably the vector comprises elements derived from disarmed strains of *Agrobacterium tumefaciens*, such as are known to those in the art.

The invention further provides a host cell containing a vector as described claimed above, or transformed with such a vector. Typically the host cell will constitute all or part of a plant protoplast, plant callus, plant tissue, developing plantlet, or immature whole plant. The plants/cells may be apple or other fruit in which the promoters are functional (e.g. tomato, melon, strawberry).

In addition, the invention provides a method of producing a transgenic plant comprising regenerating a mature plant from the transformed host cell described above.

As used herein, "transgenic" plants refer to plants or plant is compositions in which heterologous or foreign DNA is expressed or in which the expression of a gene naturally present in the plant has been altered. Such heterologous DNA will be in operative linkage with plant regulatory signals and sequences. The DNA may be integrated into a chromosome or integrated into an episomal element, such as the chloroplast, or may remain as an episomal element. In creating transgenic plants or plant compositions, any method for introduction of such DNA known to those of skill in the art may be employed. A transgenic plant comprising such a host cell, either produced as described above or by further propagation of transgenic plants forms a sixth aspect of the invention.

A further aspect of the invention provides a method of producing apples having a modified phenotype, said method comprising cultivating a transgenic apple plant described above and harvesting the fruit of the plant. The fruit itself forms yet a further aspect of the invention.

The invention will now be further described with reference to the following non-limiting examples. Further embodiments falling within the scope of the invention will occur to those skilled in the art in the light of these.

FIGURES

Figure 1B:
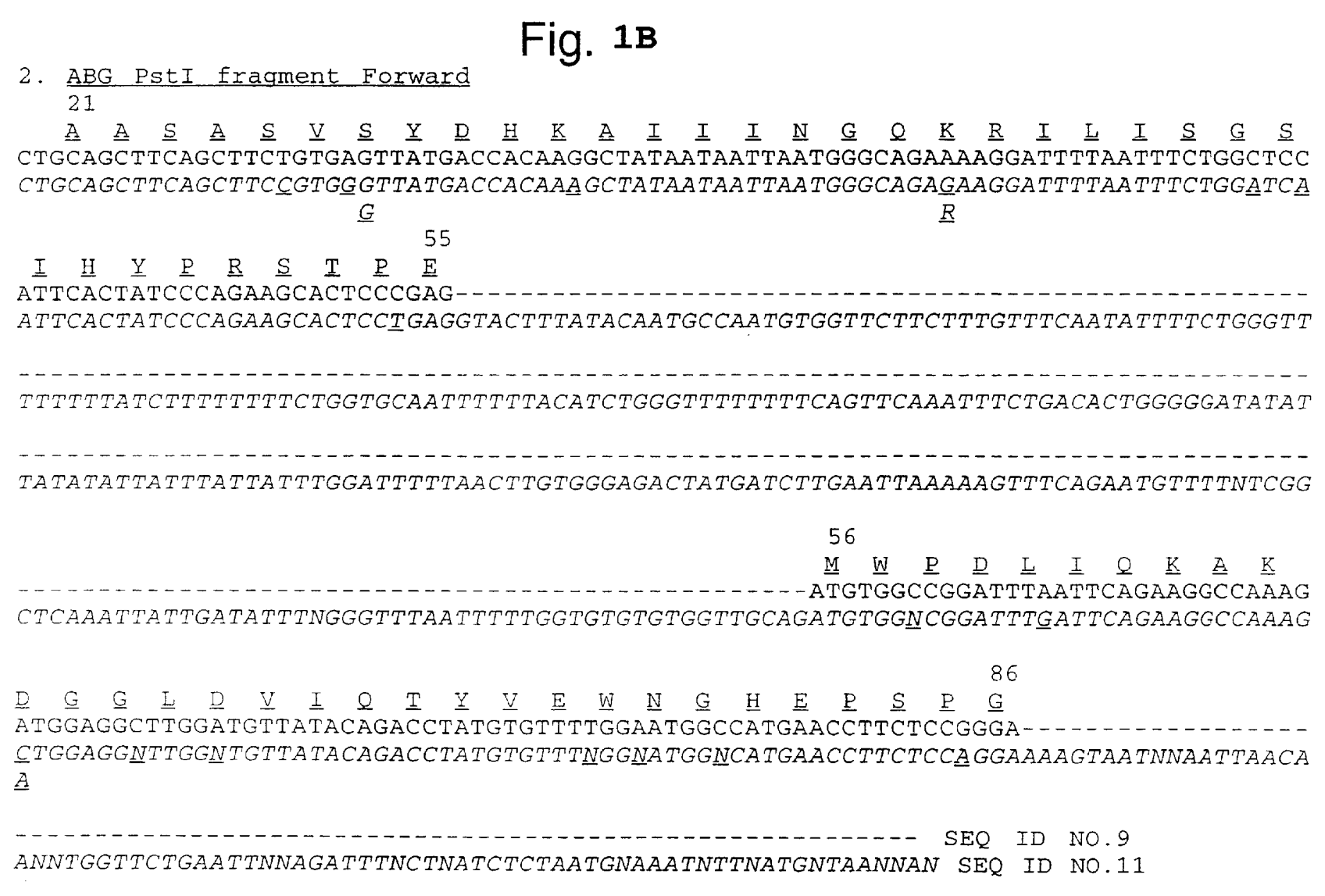

FIG. 1 shows a sequence comparison between the ABG cDNA disclosed by Ross, G. S., Wegrzyn, T-, MacRac, E-A- & Redgwell, R. J. (1994) "Apple β-galactosidase: Activity against cell wall polysaccharides and characterisation of a related cDNA clone" Plant Physiology 106: 521–528 and the EcoRI (FIG. 1(A)) and PstI fragments (FIG. 1(B)) of the genomic clone which contained the ABG1 promoter. In this figure, the upper is sequences (SEQ ID NO 8 and 9) are those of the Ross et al. cDNA. The lower sequences (SEQ ID NO 10 and No 11 respectively) in italics are those of the genomic clone. Hyphens mark gaps introduced for alignment or introns. Differences (or Ns) in the genomic sequences are double underlined and amino acid residues at intron boundaries are numbered. The uppermost line in FIG. 1 represents the amino acid sequence (SEQ ID NO: 19) encoded by the cDNA sequence. Differences in amino acid sequence are indicated beneath sequence in bold, italics and underlined.

FIG. 2 shows a sequence comparison between the ACC synthase cDNA disclosed by Lay-Yee, M & Knighton, M L 1995) "A full length cDNA encoding 1-aminocyclopropane-1-carboxylate synthase from apple" Plant Physiology 107:1017–1018 (SEQ ID NO 12) and part of the genomic clone which contained the ACC synthase promoter (SEQ ID NO 13). The uppermost line in FIG. 2 represents the amino acid sequence (SEQ ID NO: 20) encoded by the cDNA sequence.

FIG. 3 shows a sequence of a region of the ABG1 β-galactosidase gene which is upstream of the coding region incorporating a promoter sequence (SEQ ID NO 1).

FIG. 5 shows a sequence of a region of the ACC synthase gene which is upstream of the coding region incorporating a promoter sequence (SEQ ID NO 2).

FIG. 7 shows sequence features of promoters of the invention.

FIG. 8 shows the alignment of the features illustrated in FIG. 7 in the ABG1 and AAS promoters.

EXAMPLES

Figure 4A:
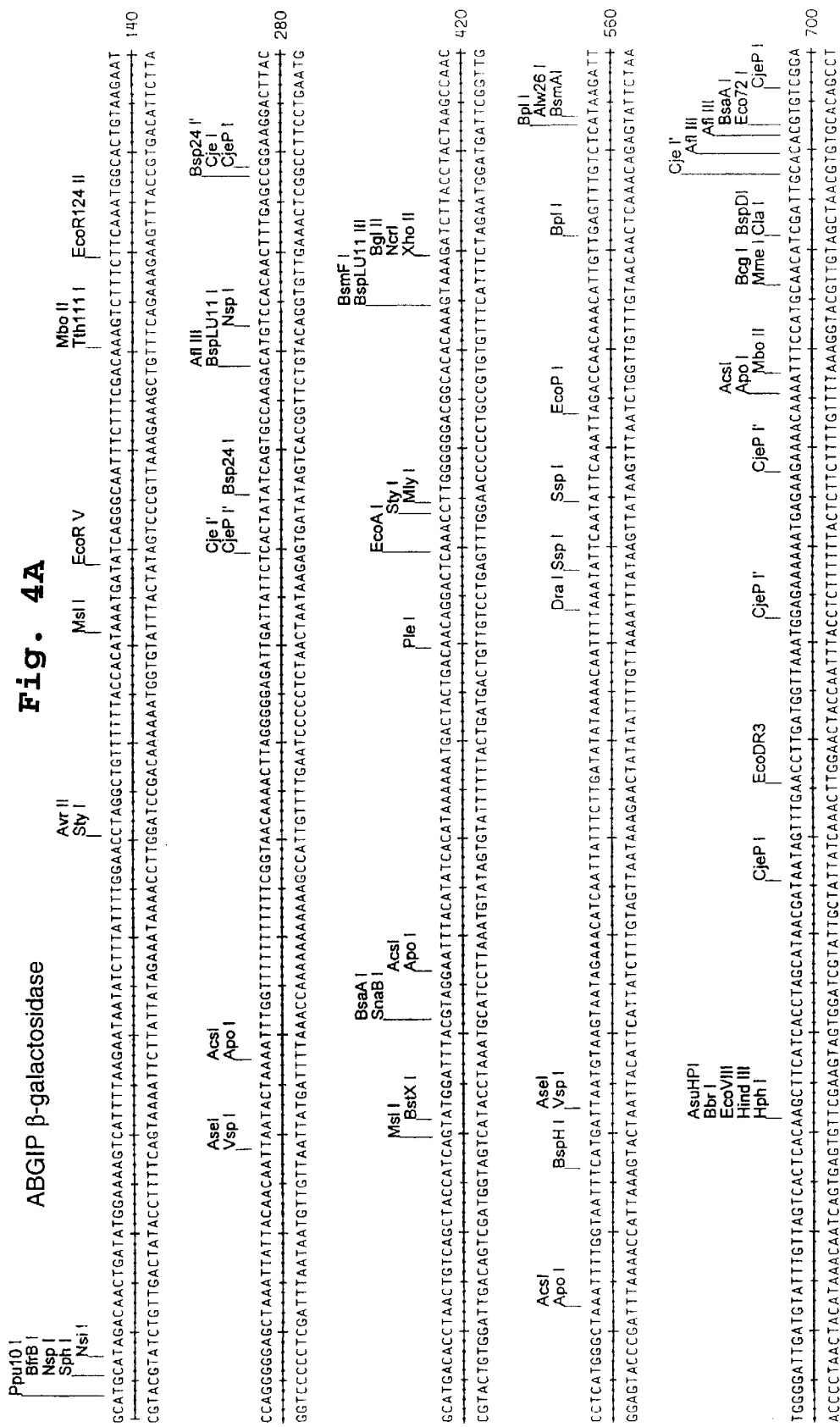
FIG. 4 shows the upstream sequence of the the ABG1 β-galactosidase gene including the promoter sequence but terminating at the start codon ATG (SEQ ID NO 14) together with its complementary strand (SEQ ID NO 15) sequence, annotated with restriction sites.
Figure 6E:
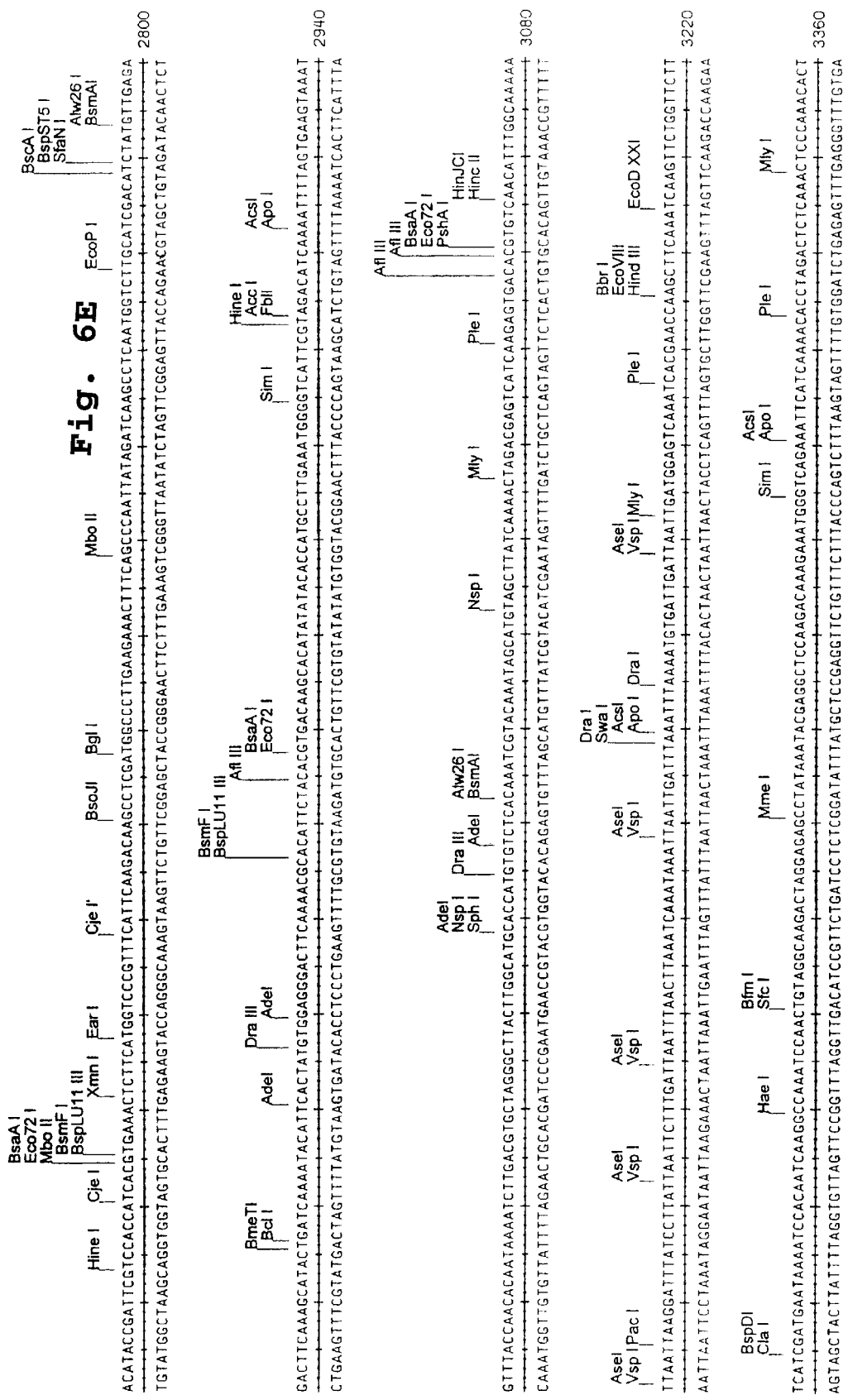
FIG. 6 shows the upstream sequence of the ACC synthase gene including the authentic promoter sequence including the start codon (ATG) from which the coding sequence has been removed (SEQ ID NO 16) and its complementary strand (SEQ ID NO 17) annotated with restriction sites.
Figure 6F:
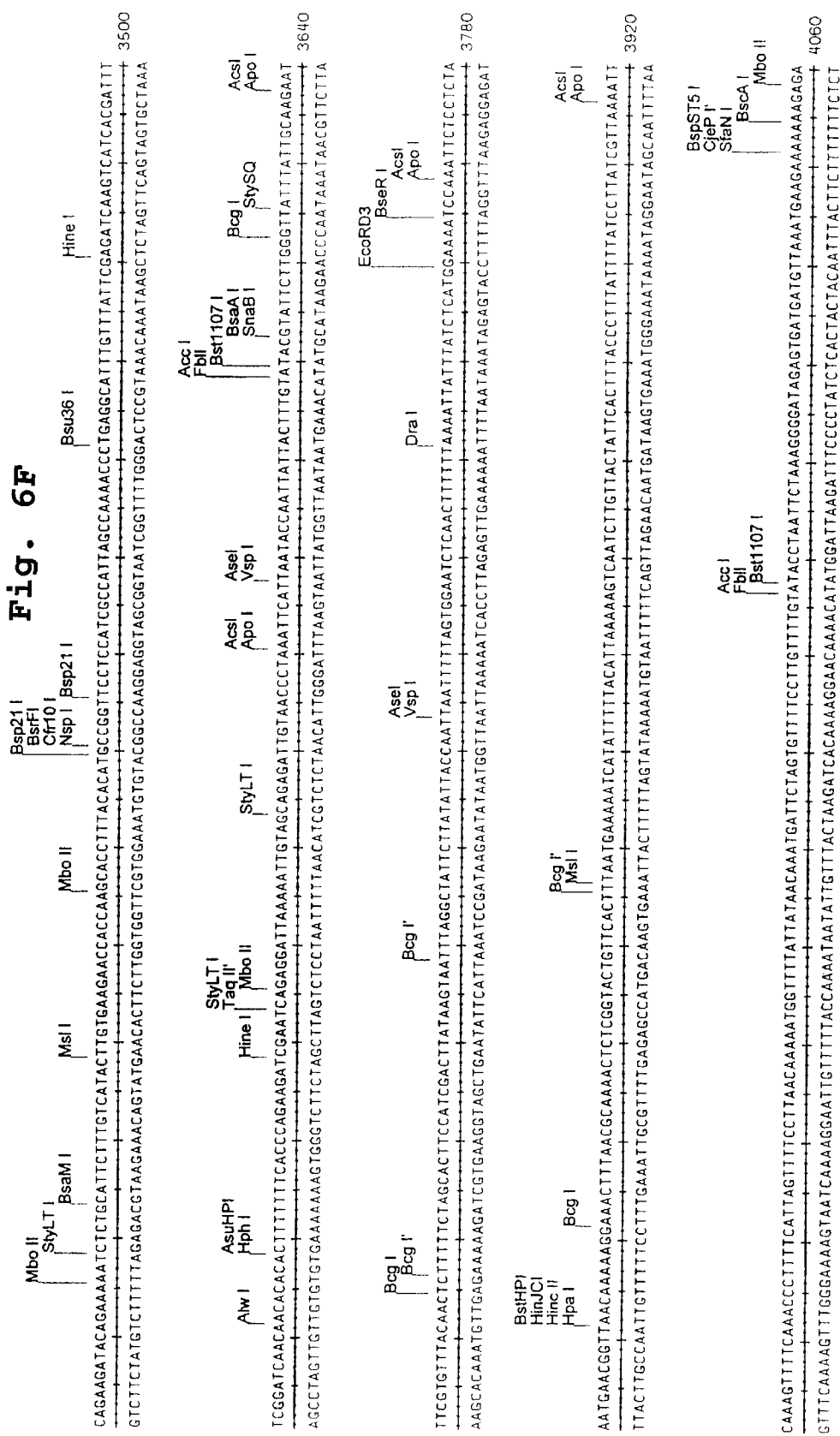

Source of Materials Used in the Isolation of Fruit-ripening-specific Promoters ABG1 β-Galactosidase cDNA
- Plant: *Malus domestica* [Borkh] cv Granny Smith
- Tissue: Mature unripe fruit cortex
- Construct: pABG1
- Vector: pBluescript II SK
- cDNA Insert: 2637 bp
- Accession: L29451
- Reference: Ross et al (1994) [supra].
- Location: The Horticulture and Food Research Institute of New Zealand Ltd., Mt- Albert Research Centre, Private Bag 92 169, Auckland, New Zealand.

ACC Synthase CDNA
- Plant: *Malus sylvestris* Mill., cv. Golden Delicious
- Tissue: ripe apple fruit mesocarp
- Construct: pAAS2
- Vector: pCGN1703
- cDNA Insert: 1636 bp
- Accession: U03294
- Reference: Dong, J.-G., Kim, W.-T., Yip, W.-K., Thompson, G. A., Li; L., Bennett, A-B. & Yang, S.-F. (1991) "Cloning of a CDNA encoding 1-aminocyclopropane-1-carboxylate synthase and expression of its MRNA in ripening apple fruit" Planta 185: 38–45 Location: Mann Laboratory, Department of Vegetable Crops, University of California/Davis, Calif. 95616, USA. Note this is practically identical to the full length Lay-Yee and Knighton clone (1995) [supra] used in the sequence comparison.

Apple Genomic Library
- Plant: Malus domestica [L] Borkh cv Mcintosh 'Wijcik'
- Tissue: Nuclei isolated from in vitro propagated apple leaves
- Vector: Lambda Gem 11 (Promega)
- Construction: Partially Sau3A digested DNA ligated to XhoI half-site vector arms
- Reference: Watillon, B., Kettmenn, R., Boxus, P. & Burny, A. (1992) "Cloning and characterization of an apple (Malus domestica [L.] Borkh) calmodulin gene" Plant Science 82:201–212 Location: Faculté des Sciences Agronomiques, Unité de Biologie Moléculaire et Physiologie Animale and Centre de Recherches Agronomiques, Station des Cultures fruitierès et maraîchères, 5030 Gembioux, Belgium.

Example 1

Procedure for the Isolation of Fruit-ripening-specific Promoters From Apples Throughout the procedure for the isolation of fruit-ripening-specific promoters, standard protocols as described by Sambrook et al (1989) "Molecular cloning: a laboratory manual ($2^{nd}$ edition)" Cold Spring Harbor Laboratory Press, were used except where indicated. DNA probe fragments were prepared by restriction digestion of plasmids containing the ABG1 and AAS (encoding ACC Synthase) cDNAs with restriction endonucleases HindII and EcoRI respectively. The ABG1 (1182 bp) and AAS (approx. 740 bp) fragments were gel purified using the BIO 101 inc. geneclean 11 kit and labelled with digoxigenin by the random priming procedure supplied by the DIG kit manufacturers (Boehringer Mannheim UK Ltd.). The apple genomic library was plated and the plaques replicated on a nylon membrane by lifting. Hybridization was performed using HYBSOL buffer (Yang et al, (1993) Nucleic Acid Research 21:3337–3338) using conditions recommended in the DIG kit protocol. The hybridization temperature was 68° C. and the post-hybridization wash conditions were stringent to ensure that only homologous DNA sequences were identified. Specific hybridization of the probes to lambda plaques containing homologous sequence was detected by chemiluminescence following the DIG kit protocol.

Single positive plaques hybridizing with the ABG1 and ACC synthase probes were identified and named λABG1 and λAAS respectively. These were purified to homogeneity by further rounds of plaque lifting and hybridization with the specific probes. The positive phages were then propagated and phage DNA was prepared from these amplified stocks using the lambda DNA purification kit from Promega Ltd. The purified DNA was digested using a panel of restriction endonucleases and the fragments resolved on an agarose get. The gel was Southern blotted onto Hybond-N Nylon (Amersham Ltd.) using standard protocols and the, blot probed with the DIG-labelled DNA fragments to identify bands containing homologous sequence. Hybridization was again detected by chemiluminescence.

Repeat large-scale digests were performed with the selected endonucleases and positive DNA bands gel purified using the geneclean II kit. The isolated bands were then cloned into the plasmid vector pGEM-3Zf(+) (Promega Ltd.). Recombinant plasmid DNA was prepared from small cultures using a plasmid miniprep. kit from QIAGEN Ltd. This DNA was used as the template for cycle sequencing reactions using the PRISM dye-terminator cycle sequencing kit from Applied Biosystems Ltd. Separate sequencing reactions of each construct using T7 and −21 M13 forward primers were performed and analyzed by the DNA sequencing service at the University of Durham (UK) using an Applied Biosystems DNA sequencer.

The sequences of each fragment combined with restriction mapping data established the identity of the genes as ABG1 and AAS and allowed the location of the cloned DNA fragments to be established (FIG. 1). To 'DNA walk' within the lambda clones to identify DNA fragments encompassing the promoter sequences, new probes were prepared from the cloned fragments. These were used to re-probe the lambda DNA Southern blots to identify large fragments predicted to cover the promoter region of each gene. These fragments were again cloned into plasmid vector pGEM3Z(f)+ and characterized by restriction mapping and sequencing of the termini.

FIG. 1 shows a sequence comparison between the ABG cDNA (SEQ ID NO 8 and 9) disclosed by Ross et al (1994) [supra] and the EcoRI and PstI fragments of the genomic clone containing the ABG1 promoter (SEQ ID NO 10 and SEQ ID NO 11 respectively). Note that the sequence 5' of the start of the cDNA sequence represents part of the region containing the promoter.

FIG. 2 shows a sequence comparison between the ACC synthase cDNA disclosed by Lay-Yee & Knighton (1995)

Plant Physiology 107:1017-1018 (Seq ID NO 12) and part of the genomic clone containing the ACC synthase promoter (SEQ ID NO 13). Note that the sequence 5' of the start of the cDNA sequence represents part of the region containing the promoter.

Deletion of small restriction fragments from these large fragments, followed by DNA sequencing allowed the determination of the sequences flanking the ATG start codon of each gene to be determined. This information was used to devise strategies to subclone the promoters to drive marker gene (gusA or uidA) expression in a plant transformation vector. The precise subcloning strategies are given below:

Subcloning Stategies

ABG1 β-Galactosidase
 a. λABG1 isolated by probing genomic library with ABG1 cDNA HindIII fragment.
 b. 5.5 kb SphI apple ABG1 genomic fragment isolated from λABG1
 c. Ligated to SphI digested pGEM3Z and obtain clone with EcoRI site of vector at the 3' end of the promoter ABG1 fragment=pGEM3ZABG1Sph(2)
 d. Digested pGEM3ZABG1Sph with PstI to excise 2.8 kb fragment containing coding sequence, and ligated to recircularise=pGEM3ZABG1SphΔPst(1)
 e. Digested pGEM3ZABG1SphΔPst with BsrDI and blunt ends with T4 pol. Then digested with EcoRI and isolated 525 bp BsrDI(blunt)/EcoRI fragment.
 f. Partially digest pGEM3ZABG1SphPst with EcoRI (2 sites present) and isolated linearized form.
 g. Digested, linearized form with SmaI to cleave downstream in the multiple cloning site and isolated band released by EcoRI cleavage within the ABG1 promoter (not the EcoRI site in the multiple cloning site).
 h. Ligated pGEM3ZABG1SphΔPst (EcoRIpartial/SmaI) with 525 bp BsrDI blunt 1EcoRI frag pABG1P (4).
 i. Digested pABG1P with SacI and SphI to release 2.7 kb ABG1 promoter fragment.
 j. Treated with T4 pol to blunt SacI and SphI ends of promoter fragment
 k. Ligated to SmaI digested pSCV1.6 and isolate recombinant carrying promoter fragment in correct orientation pSCV1.6ABG1P (6)

ACC Synthase
 a. λAAS isolated by probing genomic library with AAS cDNA EcoRI fragment. A 7 kb SacI apple AAS genomic fragment is isolated from λAAS
 b. Ligated to SacI digested pGEM3Z and obtained clone with EcoRI site of vector at the 5' end of the promoter-AAS fragment=pGEM3ZAASSac(8)
 c. Digested pGEM3ZAASSac with EcoRI and isolated 4.8 kb promoter fragment and 1.4 kb promoter-AAS coding region fragment.
 d. Ligated 1.4 kb fragment to pGEM3Z= pGEM3Z1.4kbAAS (1)
 e. Designed downstream PCR primer located just 5' to the AAS coding sequence start, incorporating a SmaI site into the primer sequence- Called AASPROM1 (5'-TTTCCCGGGTATGGATACAAGCTG-3';SEQ ID NO: 18)
 f. Used AASPROM1 primer with T7 promoter primer in a PCR using the pGEM3Z1.4kbAAS clone with the EcoRI fragment in the required orientation to produce a 300 bp fragment. Expand proofreading polymerase mixture used in PCR
 g. 300 bp frag. representing the sequence from the EcoRI site in the AAS promoter immediately 5' to the AAS coding sequence start, digested with EcoRI and SmaI.
 h. Ligated to EcoRI/SmaI digested pGEM3Z= pGEM3ZAASPCR fragment (4).
 i. Digested pGEM3ZAASPCR fragment with EcoRI and SmaI to release 300 bp AAS PCR fragment.
 j. Ligated to EcoRI/SmaI digested pSCV1.6= pSCV1.6AASPCR fragment (1).
 k. Digested pSCV1.6AASPCR fragment with EcoRI
 l. Ligated to 4.8 kb AAS EcoRI fragment and isolated recombinant carrying fragment in correct orientation to reconstruct 5.0 kb AAS promoter fragment= pSCV1.6AASP (6).

The gene regions including promoter sequences, obtained as described above, were then sequenced and the results are shown in FIGS. 3 and 5 respectively.

Example 2

Introduction of Promoters Into Plants

An efficient apple transformation system using disarmed strains of *Agrobacterium tumefaciens* carrying binary vectors (see James et al (1989) Plant Cell Reports 7:658–661; also James et al (1991) Plaint Tissue Culture Manual B8:1–18, Kluwer Academic Publishers, Netherlands), was used to produce transgenic plants of the cultivar Greensleeves in which the uidA (or gusA) marker gene (encoding β-glucuronidase—is under the control of the ABG1 and AAS promoter fragments described here.

Transgenic fruit may be analyzed for GUS activity to assess promoter activity, for instance using methods analogous to those disclosed for measuring transgene expression in fruit tissue using constitutive promoters (James et al (1996) Bio/Technology 14:56–60).

Once the ripening-specific promoters driving a useful transgene have been introduced into a commercial apple cultivar apple, the transgenic clone with the desired properties may be clonally propagated using methods well known in the art.

Example 3

Applications for Transformants

In genetically improved transgenic apple plants, the storage qualities of the fruit may be improved by the expression of transgenes driven by the ripening-specific promoters. Using antisense or co-suppression strategies to down-regulate apple genes involved in ripening (e.g. genes involved in ethylene biosynthesis or cell wall degradation), the ripening process may be delayed, thus improving the storage life of the fruit. This strategy has successfully been applied to tomatoes to produce a marketable product. To combat post-harvest losses of fruit due to fungal rots, fruit-specific expression of fungal-resistance transgenes (e.g. β-1,3-glucanases, chitinases) may be more effective than treatment with chemical fungicides because the anti-fungal molecules will be located in every cell rather than applied as a thin coating to the fruit skin. Therefore, even slightly damaged fruit will be less susceptible to rots. Such transformants will have advantages over existing systems. For instance certain traditional apple varieties have poor storage qualities (e.g. Queen Cox) which is a major com mercial drawback. Genetic manipulation using the promoters described above provides a means to control the ripening process through targeted down-regulation of the genes involved. This concept, which is impossible using existing strategies, has previously been proved only in tomato and melon. Delayed fruit ripening caused by the expression of transgenes under the control of the is fruit-specific ABG1 and AAS promoters is likely to increase the storage life of fruit and boost profits for the industry.

Another post-harvest problem is storage rot which accounts for substantial losses to the industry. At present this phenomenon is controlled to some degree by the application of chemical fungicides. As well as being expensive, these treatments are becoming less acceptable to consumers who are demanding a reduction in the use of chemicals on food. Targeted expression of non-toxic fungal-resistance factors using the fruit-specific ABG1 and AAS promoters could reduce post-harvest fruit losses and should break the reliance on chemicals to control storage rots.

What is claimed is:

1. A recombinant polynucleotide comprising a promoter sequence activated in response to ripening in fruit, which promoter is the apple β-Galactosidase (ABG1) promoter shown in nucleotides 1 to 2631 of SEQ ID No 1.

2. A replication vector comprising the polynucleotide as claimed in claim 1 which permits replication of the vector in a host cell.

3. An expression vector comprising a promoter sequence wherein said promoter sequence is the polynucleotide as claimed in claim 1.

4. The vector as claimed in claim 3, further comprising a heterologous gene operatively linked to said promoter sequence.

5. The vector as claimed in claim 4, where said heterologous gene encodes an element selected from the group consisting of (a) antisense RNA capable of down-regulating genes involved in ripening; (b) a peptide or protein improving fungal, insect, bacterial, viral, herbicidal, nematode, or arachnid resistance in plant cells, plants, or fruits; and (c) a detectable or selectable marker protein.

6. A host cell comprising the vector of claim 4.

7. A host cell comprising the vector of claim 5.

8. The host cell of either claim 6 or 7 that is a plant cell.

9. A method of identifying an apple promoter sequence that is responsive to ripening in fruit, said method comprising:

a) providing the recombinant polynucleotide of claim 1 and apple genomic DNA, b) contacting the recombinant polynucleotide and apple genomic DNA of step a) under suitable hybridization conditions, and c) identifying an apple promoter sequence that is responsive to ripening in fruit.

* * * * *

SEQUENCE LISTING

```
<160> NUMBER OF SEQ ID NOS:  20

<210> SEQ ID NO 1
<211> LENGTH: 2879
<212> TYPE: DNA
<213> ORGANISM: Malus domestica

<400> SEQUENCE: 1
gcatgcatag acaactgata tggaaaagtc attttaagaa taatatcttt attttggaac      60
ctaggctgtt ttttaccaca taaatgatat cagggcaatt tctttcgaca aagtctttct     120
tcaaatggca ctgtaagaat ccaggggag  ctaaattatt acaacaatta atactaaaat     180 ttggttttt  ttttcggta  acaaaactta gggggagatt gattattctc actatatcag     240
tgccaagaca tgtccacaac tttgagccgg aaggacttac gcatgacacc taactgtcag     300
ctaccatcag tatggattta cgtaggaatt tacatatcac ataaaaaatg actactgaca     360
acaggactca aaccttgggg ggacggcaca caaagtaaag atcttaccta ctaagccaac     420
cctcatgggc taaattttgg taatttcatg attaatgtaa gtaatagaaa catcaattat     480
ttcttgatat ataaacaat  tttaaatatt caatattcaa attagaccaa caaacattgt     540
tgagtttgtc tcataagatt tggggattga tgtatttgtt agtcactcac aagcttcatc     600
acctagcata acgataatag tttgaacctt gatggttaaa tggagaaaaa atgagaagaa     660
aacaaaattt ccatgcaaca tcgattgcac acgtgtcgga ccacgatcgg tagctagctt     720
caatgtccag agagggcact ggaaattctt tgttctggag tcaaaagtat aactgcatca     780
ctgcttgcaa gccgtacatt aaatatgtgg caacttgatc ttgatacttt ccgacaagta     840
tgaccaaaag taaagtaatt tattttaatc tttaaagaat gaatagtatt gagcaccgtc     900
caagtaaggt gattcttgta ttttccctga agcttaattt tactattgtc ttgtgacttt     960
tgtacacata tcaatttaga cttttccgta agggtaaatg gaaaatcaag cttaaagtca    1020
tgaaaaccaa caaacctatt tattgttttt cgattcttga taaattctcg tatgttattg    1080
gttgtatagg atcttgtgta tatcgtttca ttacctgaaa agtataaaca cataattata    1140
tataaggaaa actaatgaaa atgatttgaa aactttgagt tttaacgata aagacaaaat    1200
aaagggtaaa gtgaatagta caaggattga cttttttagtg taaaaatgtg attttttcgtt   1260 aagtgaacag taccgggaac ttttcattaa agttcccgca tgaaacacac tttttttttt   1320
aaggtgataa aggatttcgt tcataattaa cgaaatgaac taatacagag agcatggata    1380
agaagtggcc ttgaaaaacc tcgtcctaag taatccacat aaaaaaaact ttgagagaga    1440
aaaaatagca acccatgcta gaaacagaac acatcacgtt aaagtataat catcaaacac    1500
acaacttatt agctaagaaa agatattggg tgaatgatga ttaaatgaaa ataaaataag    1560
```

-continued

| | |
|---|---|
| aaaaacagaa atcggattgg atgatttaag acaaataaaa ggaaaaaaat cgatcgatca | 1620 |
| ccttatccta taacaaaaaa ttggaatcct tcatttttag atgtctaaat atatacatga | 1680 |
| aaaggaaatc cttatccata ttaatatggt ttggtagtgt ttttattat ttacaaattt | 1740 |
| cttttgtttg gtcccaaagg ggaacaattt ttaatagatt cgtttaccgg catggataga | 1800 |
| cccatgcaaa gcttttcttc aaatatctga ttgacacatc aatttagaaa ttgagtaaca | 1860 |
| tctctatcaa atgaaaactt catattgcaa atcacatttc cttaattta gcaaacagaa | 1920 |
| aaaggaaatt gaaggataa gctcaaataa tttcataaat tgttaaaact gaatcaaaag | 1980 |
| ttcgtttgat tgccttgatt tcgcgagaaa atgcttaccc tcgtaaaaaa aagaatcatg | 2040 |
| tcgtttaaat aagtttgatt tggacgtttt gacggttttt tgtcaactct tatagaagtt | 2100 |
| tcatcaaatg tcaatgatag aataacatct tagctaggat ttcgtgttcc acatgtatat | 2160 |
| acaatacata agcataaatt agaaagttca tcttttaaga atccaaatcc tcgaaggttc | 2220 |
| tccatcgagg aatcctattc catataggaa acggaattcc ttattccaca tgtattacac | 2280 |
| aaacataaat taggaagttc tttctctcct aggaatccaa atcctcaaag gttttccctc | 2340 |
| tctaaggaat cctattcctc atagccttgc gacgtttata tatacggatt caccatacaa | 2400 |
| atgaaataca acagatacag tattttctac agacacccgt atttccaaaa atgtgagaga | 2460 |
| gcttgttcaa ggcagcagaa gtggcccccc ccccttccct ttgcagtttg cacatttgca | 2520 |
| atcttcatct tcaaaacctt atataaagca gtagcgggag caacacgttc cttgcacaac | 2580 |
| cattgaacca aaccataaac tttctcaccc gtgaaatcca gcagtacact tctctactct | 2640 |
| gccaccccct ttctgtctct tttccgaata ccaaaagcac caaccaaaga aaccaaatcc | 2700 |
| aaatcccaaa acccaaaaaa ataaatatgt attattcaag ttttttgatac aaacaaaagc | 2760 |
| aaatatatat attataaagg ccattgcttt tgagattttc agaagcaggg gacaaatggg | 2820 |
| tgttggaagt caaacaatgt ggagcattct gctactgctt tcctgcattt tttctgcag | 2879 |

<210> SEQ ID NO 2
<211> LENGTH: 5391
<212> TYPE: DNA
<213> ORGANISM: Malus domestica

<400> SEQUENCE: 2

| | |
|---|---|
| gagctcgtta aataaaatat ttgatttcta aaaaaatgg accccctaaa taaagtattt | 60 |
| ggattctaga tataatatct ctttcttttt gttattatat tttcaatata attattagtt | 120 |
| cggtgataga tattagttat ttggttttca gtgtatggag attagttgtt taatttgtgt | 180 |
| ataattattc ttcatttgtt tttgttaaat gtaatttttt ttttcaaaaa tttatttgta | 240 |
| attggtatct ctggatttta ctaactagtt tgtgtgtttt ctttataatg ctaaactgct | 300 |
| aattgcttga aactttata gttgcatgca tattctagtt ttgaagtaag gtatgaaact | 360 |
| agtatttag atgcaatggg taagttgatg atataaatga gtcatctttt gaaagtcttc | 420 |
| tttttaattt atctgataat agtttgtcac aagactcgtt tggaagtact tttaaaatga | 480 |
| ctgaaagcac ttttggtgaa attgattttg gttccaaaag cgtgcttttt ggaagaagca | 540 |
| tcaggtattt gcttctatac ttcttgtaga agcactttta agtgcttttc catgatgcac | 600 |
| ttgaatttt attgaagatt ggtttcaaaa acattttcac taaaagcgct ttcaaacatt | 660 |
| ttaaaaacac ttccaaacga acccataata gaaggaaatt tatagtacct ttttttattaa | 720 |
| ttcataaata atctaatgtt aaatcctttg aaagtatata gtgtatataa tttcatggaa | 780 |
| tcataattaa cagaagtatt gagatgaata cattgatggg agaatgggcc ttgcatcaaa | 840 |

```
ctataagttg ggttattccc tatattattg attgatttta tggtggatcc tcaaatttgt    900
catgatatca tagcaagttg acccatgtgt aatagtgaac aacaccatgc aacaatcctc    960
gcaaccagta gtggcccttg tagcgaggca ataaccctttg cagccggtag cagtgtgcgg   1020
cagtcaatgc catggcagtg cagcacgaag aagcagccat aacagtgcaa cacgtagaaa   1080
gcagtgcagc aaggcagcag cggtgcaaca acaagcaatg cagtgtacaa tagtggcaaa   1140
aatgcaactg gcaatgcaaa cattagcgag tgagtcgaca agcaatgcga acattaacgt   1200
gacataagat ggatttcggt catccaaggt tatttaggcc atctccaacc gaaggaagca   1260
agagggcttg ttttagccct ttggccctcc aagaatataa tattttaatg aatagtgcaa   1320
ggctatattt cttaccatat ccaaccaagg ggccaaagaa ccataggcca acatagccc    1380
tgtgacaaaa aatcatctcc aaccgaggtc caaagagtca tagggccaaa cataatttat   1440
tattttaatt gaattactat ggttacttaa attaaattac ctcaataatt ttatgttatg   1500
gattgtcaat aattttcatg ttgttaaatg ttttaaaaaa tgttgtttaa atttcatatt   1560
gttaattttt ttttatgttg tttaatgtta cttaatgtta tttaatgttg tttaatattg   1620
tttaatgttg tttcatgtta cttaatgtca cttaatgttg tttaatgact taggaagtta   1680
taggaaaaaa atagaatttt taatttttt ttaattttgt aaaataaaaa aattaaatat    1740
gatgtcaaca tgtggcttgg cccaaggctg gcttgttggc gaggttgggc caaccagttg   1800
gcccttggc ccttttttgt ccaatggggc ccacaagcct tttggcctag ccctcggttg    1860
gagacagttt tcggtctatt ttcggccctc tagccctctg gactatttgg ttggagatgg   1920
ctttagaccc caaaaactgc gttttagaaa atttacaaac ttttcatttt tgtccgatcc   1980
actttcatta ccctccctag agcttcccta cattcgcaga gtagttttga gtcattacac   2040
tttataattc accacattcc cgaaggaaga actaagtcta ataaagcttt atggagccaa   2100
ataggtaaag tgtgtgcatc tctgccaaag gaaaatagaa ggcttcaaat cacaagtcta   2160
aaagaagagg agaggcttca aattaaatta caagtccgtc tcatagggtc ctcatatgcc   2220
tattcattca tttcatatta acggtggtag cctaaataag cacgaaagcg ttcactttga   2280
gaggctttaa accataagtt tgtgaaccat gtttcatagc tcacacttgt gttcttcatc   2340
aagttcatgg agaattacca agcacaacaa atacatgtgt tggttcatcc acattaaagt   2400
cgaagattgc ccgccacatg aaactcctgg tggtcccatt cattcaagat caaacctcga   2460
cgacccctaa agaaattata agtctaattc aagaccaaga gtacaccacc cttgaataaa   2520
attcgctcta gaggaatgaa gtaaatccaa acctttggag gaaaccagaa agctctttgc   2580
ccaaagaaaa cattataatt cttcatcaag cttgtgagaa ttcaacaagc acaaaaaaaa   2640
aaaaaaaaaa aaaaaaaaac acataccgat tcgtccacca tcacgtgaaa ctcttcatgg   2700
tcccgtttca ttcaagacaa gcctcgatgg cccttgaaga aactttcagc ccaattatag   2760
atcaagcctc aatggtcttg catcgacatc tatgttgaga gacttcaaag catactgatc   2820
aaaatacatt cactatgtgg agggacttca aaacgcacat tctacacgtg acaagcacat   2880
atatacacca tgccttgaaa tggggtcatt cgtagacatc aaaattttag tgaagtaaat   2940
gtttaccaac acaataaaat cttgacgtgc tagggcttac ttggcatgca ccatgtgtct   3000
cacaaatcgt acaaatagca tgtagcttat caaaactaga cgagtcatca agagtgacac   3060
gtgtcaacat ttggcaaaaa ttaattaagg atttatcctt attaattctt tgattaattt   3120
aacttaaatc aaataaatta attgatttaa atttaaaatg tgattgatta attgatggag   3180
```

```
tcaaatcacg aaccaagctt caaatcaagt tctggttctt tcatcgatga ataaaatcca    3240
caatcaaggc caaatccaac tgtaggcaag actaggagag cctataaata cgaggctcca    3300
agacaaagaa atgggtcaga aattcatcaa acacctaga ctctcaaact cccaaacact     3360
cagaagatac agaaaaatct ctgcattctt tgtcatactt gtgaagaacc accaagcacc    3420
tttacacatg ccggttcctc catcgccatt agccaaaacc ctgaggcatt tgtttattcg    3480
agatcaagtc atcacgattt tcggatcaac aacacacact ttttttcacc cagaagatcg    3540
aatcagagga ttaaaaattg tagcagagat tgtaaccctt aattcattaa taccaattat    3600
tactttgtat acgtattctt gggttattta ttgcaagaat ttcgtgttta caactctttt    3660
tctagcactt ccatcgactt ataagtaatt taggctattc ttatattacc aattaatttt    3720
tagtggaatc tcaactttt taaaattatt tatctcatgg aaaatccaaa ttctcctcta     3780
aatgaacggt taacaaaaag gaaactttaa cgcaaaactc tcggtactgt tcactttaat    3840
gaaaaatcat attttacat taaaaagtca atcttgttac tattcacttt accctttatt     3900
ttatccttat cgttaaaatt caagttttc aaacccttttt cattagtttt ccttaacaaa    3960
aatggtttta ttataacaaa tgattctagt gttttccttg ttttgtatac ctaattctaa    4020
aggggataga gtgatgatgt taaatgaaga aaaaagaga gatgccattt tgttcgtac     4080
cggattttcg aggttgactc aaatcaaaac attgtttggt aattggagta atgaactgag    4140
cagacataaa aacctgtgcg aacttaaagg ttaaaaaaa ggttaaaaaa aaaaaactta     4200
aacgaaaaaa tctcagtatt gtttatttta acaaaaaatc acacttttac attaaaaagt    4260
caatcctgtt attatttatt ttaccccttta ttttgtttaa aactcaaagt ttttaagtat   4320
ttttcattaa ttttccttaa aaaaaataga aagtgagaaa aatgcccgac aaaattagtt    4380
gtggctacta gagtcaagaa gcatatggac cagggtgggt cgctcttggc attttctatg    4440
atacttgttg tcggtaaggt tttgtaaaca aaactagacc cgagtattaa ttcttgtttc    4500
tttgtttttt tttcaattac aagccgatta atgcttctat gtacacttat aatccccacg    4560
caagtttgta ggttatgcca ggtaatggtg aacgccctac ccacttccca gtccaagcaa    4620
atagtgagaa aataaattaa tggatgatac taggaaaatt aaatttggag ataaaatttg    4680
caaattatat aaatatgtcac ctatacgaat taacacattt atcaatatttt aaataataaa   4740
tcaatcatca actaccatat aatttagttt ccaaaatttt atttacaaat ttagtctttta   4800
gtattaccct caattaatta tttaatgttg attagtaaac actaaaactt cattgctttg    4860
ggatttggga gtgtctgaag gtccttcatg atcaatgtct ttagatggtg gagcaaaagc    4920
gcgtacaatt aattatcatg ttgttttttgg atttttattg aatcaaaata cttggatcat   4980
aatgttaaga aaagaaccaa gagaaatcta aagagacttt cttaaaaatg agattcttca    5040
taattttattt atcatgtttt tggtacaata tttataatat cggggcaaaa attaatgtta   5100
aaatgtaaga taacagagaa ttcatagaaa gcacaatttt aagataatct ccttaacatt    5160
tataaaaaat atgactactc agtgtgacgt gtcattcctt tgttagacaa ataatttcta    5220
tatatttaaa tttatattat tactttttttg ctatatatag acccctccag tccaacaaca   5280
tccaatatcc cacttcaaac ttgtaatcca aaaccaaaac ctcaaactct ctctctattg    5340
ctttctcttc ctttccacac ttctttctta cagcttgtat ccatacccgg g            5391

<210> SEQ ID NO 3
<211> LENGTH: 156
<212> TYPE: DNA
<213> ORGANISM: Malus domestica
```

<400> SEQUENCE: 3

```
ggaaacttta acgcaaaact ctcggtactg ttcactttaa tgaaaaatca tatttttaca      60
ttaaaaagtc aatcttgtta ctattcactt tacccttat  tttatcctta tcgttaaaat    120
tcaaagtttt caaacccttt tcattagttt tcctta                              156
```

<210> SEQ ID NO 4
<211> LENGTH: 155
<212> TYPE: DNA
<213> ORGANISM: Malus domestica

<400> SEQUENCE: 4

```
gggaacttta atgaaaagtt cccggtactg ttcacttaac gaaaaatcac attttttacac    60
taaaaagtca atccttgtac tattcacttt acccttttatt ttgtctttat cgttaaaact  120
caaagttttc aaatcatttt cattagtttt cctta                              155
```

<210> SEQ ID NO 5
<211> LENGTH: 227
<212> TYPE: DNA
<213> ORGANISM: Malus domestica

<400> SEQUENCE: 5

```
ttcgtttgga agtgttttta aaatgtttga aagcgctttt agtgaaaatg tttttgaaac     60
caatcttcaa taaaaattca agtgcatcat ggaaaagcac ttaaagtgct ttctacaaga   120
agtatagaag caaatacctg atgcttcttc caaaaagcac gcttttggaa ccaaaatcaa   180
tttcaccaaa agtgctttca gtcattttaa agtacttcc aaacgag                  227
```

<210> SEQ ID NO 6
<211> LENGTH: 217
<212> TYPE: DNA
<213> ORGANISM: Malus domestica

<400> SEQUENCE: 6

```
ctcgtttgaa attgttttta aataactga  aaacatttttt gataaaatgt tttagaatc     60
aatctttagt agaaatagat gtgaatattg aaaaagcact tcaaatgctt tctacaagaa   120
gcacgtgttt cttgcagaaa acacctcagg tgcttttgaa atccaaaaaa attattttaa   180
agcattttca gtcattttaa aaacacttcc aaatgag                            217
```

<210> SEQ ID NO 7
<211> LENGTH: 28
<212> TYPE: DNA
<213> ORGANISM: Malus domestica

<400> SEQUENCE: 7

```
gaaaaatcac atttttttaca ctaaaaag                                      28
```

<210> SEQ ID NO 8
<211> LENGTH: 177
<212> TYPE: DNA
<213> ORGANISM: Malus domestica

<400> SEQUENCE: 8

```
ctcaactctg ccactctctc tctgtctctt tccaaaatat caaaagcacc aaacaaaaga    60
aaccaaattc aaatcccaaa acacaatata tattttaagt ttttggtaca aacaaagcaa  120
gtatatttat atataaaggc cattgctttt gagcgtttca gaagcaaggg aaaaatg      177
```

<210> SEQ ID NO 9
<211> LENGTH: 200
<212> TYPE: DNA
<213> ORGANISM: Malus domestica
<220> FEATURE:
<221> NAME/KEY: CDS
<222> LOCATION: (3)..(200)

<400> SEQUENCE: 9

```
ct gca gct tca gct tct gtg agt tat gac cac aag gct ata ata att      47
   Ala Ala Ser Ala Ser Val Ser Tyr Asp His Lys Ala Ile Ile Ile
    1               5                  10                  15 aat ggg cag aaa agg att tta att tct ggc tcc att cac tat ccc aga     95
Asn Gly Gln Lys Arg Ile Leu Ile Ser Gly Ser Ile His Tyr Pro Arg
                20                  25                  30 agc act ccc gag atg tgg ccg gat tta att cag aag gcc aaa gat gga   143
Ser Thr Pro Glu Met Trp Pro Asp Leu Ile Gln Lys Ala Lys Asp Gly
            35                  40                  45 ggc ttg gat gtt ata cag acc tat gtg ttt tgg aat ggc cat gaa cct   191
Gly Leu Asp Val Ile Gln Thr Tyr Val Phe Trp Asn Gly His Glu Pro
        50                  55                  60 tct ccg gga                                                       200
Ser Pro Gly
    65
```

<210> SEQ ID NO 10
<211> LENGTH: 561
<212> TYPE: DNA
<213> ORGANISM: Malus domestica
<220> FEATURE:
<221> NAME/KEY: misc_feature
<222> LOCATION: (397, 421, 440, 447, 501, 506, 511, 513, 521, 523, 536)
<223> OTHER INFORMATION: n = uncertain

<400> SEQUENCE: 10

```
gattcttatt ccacatgtat tacacaaaca taaattagga agttcttcct ctcctaggaa    60
tccaaatcct caaggttttt ccctctctaa ggaatcctat tcctcatagc cttgcgacgt   120
ttatatatac ggattcacca tacaaatgaa atacaacaga tacagtattt tctacagaca   180
cccgtatttc caaaaatgtg agagagcttg ttcaaggcag cagaagtggc ccccccccct   240 tcccttttgca gtttgcacat ttgcaatctt catcttcaaa accttattta aagcagtagc   300
gggagcaaca cgttccttgc acaaccattg aaccaaacca taaactttct cacccgtgaa   360
atccagcagt acacttctct actctgccac ccccttnctg tctcttttcc gaataccaaa   420
ngcaccaacc aaagaaacan ttccaantcc caaacccaaa aaaataaata tgtattattc   480
aagttttggg tacaaacaaa ngcaanttat ntntattatt nanggccatt gctttnggga   540
ttttcagaag caggggacaa a                                             561
```

<210> SEQ ID NO 11
<211> LENGTH: 537
<212> TYPE: DNA
<213> ORGANISM: Malus domestica
<220> FEATURE:
<221> NAME/KEY: misc_feature
<222> LOCATION: (316, 339, 376, 408, 413, 436, 439, 444, 471..472, 482..
    483)
<223> OTHER INFORMATION: n = uncertain
<221> NAME/KEY: misc_feature
<222> LOCATION: (496..497, 504, 507, 518, 523, 526, 530, 534..535, 537)
<223> OTHER INFORMATION: n = uncertain

<400> SEQUENCE: 11

```
ctgcagcttc agcttccgtg ggttatgacc acaaagctat aataattaat gggcagagaa      60
ggattttaat ttctggatca attcactatc ccagaagcac tcctgaggta ctttatacaa     120
tgccaatgtg gttcttcttt gtttcaatat tttctgggtt tttttttatct tttttttctg    180 gtgcaatttt ttacatctgg gttttttttc agttcaaatt tctgacactg ggggatatat    240
tatatattat ttattatttg gatttttaac ttgtgggaga ctatgatctt gaattaaaaa     300
gtttcagaat gttttntcgg ctcaaattat tgatatttng ggtttaattt ttggtgtgtg    360
tggttgcaga tgtggncgga tttgattcag aaggccaaag ctggaggntt ggntgttata    420
cagacctatg tgtttnggna tggncatgaa ccttctccag gaaaagtaat nnaattaaca    480
anntggttct gaattnnaga tttnctnatc tctaatgnaa atnttnatgn taannan       537
```

<210> SEQ ID NO 12
<211> LENGTH: 264
<212> TYPE: DNA
<213> ORGANISM: Malus domestica
<220> FEATURE:
<221> NAME/KEY: CDS
<222> LOCATION: (100)..(264)

<400> SEQUENCE: 12

```
atccaaaacc aaaacctcaa actctctctc tattgctttc tcttcctttc cacacttctt      60
tcttacagct tgtatccata cacaagaaaa ttaaccaaa atg cgc atg tta tcc         114
                                             Met Arg Met Leu Ser
                                               1             5 aga aac gct acg ttc aac tct cac ggc caa gac tcc tcc tac ttc tta      162
Arg Asn Ala Thr Phe Asn Ser His Gly Gln Asp Ser Ser Tyr Phe Leu
              10                  15                  20 ggt tgg caa gag tat gag aag aac ccc tac cat gag gtc cac aac aca      210
Gly Trp Gln Glu Tyr Glu Lys Asn Pro Tyr His Glu Val His Asn Thr
         25                  30                  35 aac ggg att att cag atg ggt cta gca gaa aat cag ctc tgt ttt gat      258
Asn Gly Ile Ile Gln Met Gly Leu Ala Glu Asn Gln Leu Cys Phe Asp
     40                  45                  50 ctt ctc                                                               264
Leu Leu
    55
```

<210> SEQ ID NO 13
<211> LENGTH: 775
<212> TYPE: DNA
<213> ORGANISM: Malus domestica
<220> FEATURE:
<221> NAME/KEY: misc_feature
<222> LOCATION: (1,13, 18, 22, 41, 47, 96, 118, 128..130, 134, 137, 181)
<223> OTHER INFORMATION: n = uncertain
<221> NAME/KEY: misc_feature
<222> LOCATION: (199, 202, 235, 240, 262, 264, 274, 338, 380, 416, 418)
<223> OTHER INFORMATION: n = uncertain
<221> NAME/KEY: misc_feature
<222> LOCATION: (420, 422, 426, 432, 434, 450, 514, 524, 526, 624)
<223> OTHER INFORMATION: n = uncertain

<400> SEQUENCE: 13

```
naggggggaa canttaantt tcaggtggtt gnggattttt nagggantca aaaaagttgg      60
atcataatgt taggaaaggg aaccaggaat tttaangaga tttttaaaa aggagattnt     120 tcataatnnn tttnttnagg tttgggggac aatatttata atatgggggg caaaaattaa    180
ngttaaaatg taagataana gngaattcat agaaggcaac aattttaaga taatntcctn    240
aacatttata aaaaatatga anantcagtg ggangtgtca ttcccttttgt tagacaaata   300
```

-continued

| | |
|---|---|
| atttctatat atttaaattt atattattac tttttgnta tatatagacc cctccagtcc | 360 |
| aacaacatcc aatatcccan ttcaaacttg taatccaaaa ccaaaacctc aaactntntn | 420 |
| tntatngctt tntnttcctt tccacacttn tttcttacag cttgtatcca tacacaagaa | 480 |
| aattaaccaa aatgcgcatg ttatccagaa acgntacgtt caantntcac ggccaagact | 540 |
| cctcctactt cttaggttgg caagagtatg agaagaaccc ctaccatgag gtccacaaca | 600 |
| caaacgggat tattcagatg ggtntagcag aaaatcaggt aattaattat tataatttac | 660 |
| gagcttaatt ttttattact accatgcata tatgttacca tatgtagtta tatttagtat | 720 |
| ataaactttg tgcgcgtttc aatatttttt ttttctagct ctgttttgtc ttctc | 775 |

<210> SEQ ID NO 14
<211> LENGTH: 2818
<212> TYPE: DNA
<213> ORGANISM: Malus domestica

<400> SEQUENCE: 14

| | |
|---|---|
| gcatgcatag acaactgata tggaaaagtc attttaagaa taatatcttt attttggaac | 60 |
| ctaggctgtt ttttaccaca taaatgatat caggggcaatt tctttcgaca aagtctttct | 120 |
| tcaaatggca ctgtaagaat ccaggggggag ctaaattatt acaacaatta atactaaaat | 180 |
| ttggttttttt tttttcggta acaaaactta gggggagatt gattattctc actatatcag | 240 |
| tgccaagaca tgtccacaac tttgagccgg aaggacttac gcatgacacc taactgtcag | 300 |
| ctaccatcag tatggattta cgtaggaatt tacatatcac ataaaaaatg actactgaca | 360 |
| acaggactca aaccttgggg ggacggcaca caaagtaaag atcttaccta ctaagccaac | 420 |
| cctcatgggc taaattttgg taatttcatg attaatgtaa gtaatagaaa catcaattat | 480 |
| ttcttgatat ataaaacaat tttaaatatt caatattcaa attagaccaa caaacattgt | 540 |
| tgagtttgtc tcataagatt tggggattga tgtatttgtt agtcactcac aagcttcatc | 600 |
| acctagcata acgataatag tttgaacctt gatggttaaa tggagaaaaa atgagaagaa | 660 |
| aacaaaattt ccatgcaaca tcgattgcac acgtgtcgga ccacgatcgg tagctagctt | 720 |
| caatgtccag agagggcact ggaaattctt tgttctggag tcaaaagtat aactgcatca | 780 |
| ctgcttgcaa gccgtacatt aaatatgtgg caacttgatc ttgatacttt ccgacaagta | 840 |
| tgaccaaaag taaagtaatt tattttaatc tttaaagaat gaatagtatt gagcaccgtc | 900 |
| caagtaaggt gattcttgta ttttccctga agcttaattt tactattgtc ttgtgacttt | 960 |
| tgtacacata tcaatttaga cttttccgta agggtaaatg gaaaatcaag cttaaagtca | 1020 |
| tgaaaaccaa caaacctatt tattgttttt cgattcttga taaattctcg tatgttattg | 1080 |
| gttgtatagg atcttgtgta tatcgtttca ttacctgaaa agtataaaca cataattata | 1140 |
| tataaggaaa actaatgaaa atgatttgaa aactttgagt tttaacgata aagacaaaat | 1200 |
| aaagggtaaa gtgaatagta caaggattga cttttttagtg taaaaatgtg attttttcgtt | 1260 |
| aagtgaacag taccgggaac ttttcattaa agttcccgca tgaaacacac tttttttttt | 1320 |
| aaggtgataa aggatttcgt tcataattaa cgaaatgaac taatacagag agcatggata | 1380 |
| agaagtggcc ttgaaaaacc tcgtcctaag taatccacat aaaaaaaact ttgagagaga | 1440 |
| aaaaatagca acccatgcta gaaacagaac acatcacgtt aaagtataat catcaaacac | 1500 |
| acaacttatt agctaagaaa agatattggg tgaatgatga ttaaatgaaa ataaaataag | 1560 |
| aaaaacagaa atcggattgg atgatttaag acaaataaaa ggaaaaaaat cgatcgatca | 1620 |
| ccttatccta taacaaaaaa ttggaatcct tcattttttag atgtctaaat atatacatga | 1680 |

-continued

```
aaaggaaatc cttatccata ttaatatggt ttggtagtgt tttttattat ttacaaattt    1740
cttttgtttg gtcccaaagg ggaacaattt ttaatagatt cgtttaccgg catggataga    1800
cccatgcaaa gcttttcttc aaatatctga ttgacacatc aatttagaaa ttgagtaaca    1860
tctctatcaa atgaaaactt catattgcaa atcacatttc cttaatttta gcaaacagaa    1920
aaaggaaatt gaaggataa gctcaaataa tttcataaat tgttaaaact gaatcaaaag     1980
ttcgtttgat tgccttgatt tcgcgagaaa atgcttaccc tcgtaaaaaa aagaatcatg    2040
tcgtttaaat aagtttgatt tggacgtttt gacggttttt tgtcaactct tatagaagtt    2100
tcatcaaatg tcaatgatag aataacatct tagctaggat ttcgtgttcc acatgtatat    2160
acaatacata agcataaatt agaaagttca tcttttaaga atccaaatcc tcgaaggttc    2220
tccatcgagg aatcctattc catataggaa acggaattcc ttattccaca tgtattacac    2280
aaacataaat taggaagttc tttctctcct aggaatccaa atcctcaaag gttttccctc    2340
tctaaggaat cctattcctc atagccttgc gacgtttata tatacggatt caccatacaa    2400
atgaaataca acagatacag tattttctac agacacccgt atttccaaaa atgtgagaga    2460
gcttgttcaa ggcagcagaa gtggcccccc ccccttccct ttgcagtttg cacatttgca    2520
atcttcatct tcaaaacctt atataaagca gtagcgggag caaacgttc cttgcacaac     2580 cattgaacca aaccataaac tttctcaccc gtgaaatcca gcagtacact tctctactct    2640 gccacccct ttctgtctct tttccgaata ccaaaagcac caaccaaaga aaccaaatcc     2700
aaatcccaaa acccaaaaaa ataaatatgt attattcaag ttttttgatac aaacaaaagc    2760 aaatatatat attataaagg ccattgcttt tgagattttc agaagcaggg gacaaatg      2818
```

<210> SEQ ID NO 15
<211> LENGTH: 2818
<212> TYPE: DNA
<213> ORGANISM: Malus domestica

<400> SEQUENCE: 15

```
catttgtccc ctgcttctga aaatctcaaa agcaatggcc tttataatat atatatttgc      60
ttttgtttgt atcaaaaact tgaataatac atatttattt ttttgggttt tgggatttgg     120
atttggtttc tttggttggt gcttttggta ttcggaaaag agacagaaag ggggtggcag     180
agtagagaag tgtactgctg gatttcacgg gtgagaaagt ttatggtttg gttcaatggt     240
tgtgcaagga acgtgttgct cccgctactg ctttatataa ggttttgaag atgaagattg     300
caaatgtgca aactgcaaag ggaagggggg ggggccactt ctgctgcctt gaacaagctc     360
tctcacattt ttggaaatac gggtgtctgt agaaaatact gtatctgttg tatttcattt     420
gtatggtgaa tccgtatata taaacgtcgc aaggctatga ggaataggat tccttagaga    480
gggaaaacct ttgaggattt ggattcctag gagagaaaga acttcctaat ttatgtttgt     540
gtaatacatg tggaataagg aattccgttt cctatatgga ataggattcc tcgatggaga    600
accttcgagg atttggattc ttaaaagatg aactttctaa tttatgctta tgtattgtat     660
atacatgtgg aacacgaaat cctagctaag atgttattct atcattgaca tttgatgaaa    720
cttctataag agttgacaaa aaccgtcaa acgtccaaa tcaaacttat ttaaacgaca       780
tgattctttt ttttacgagg gtaagcattt tctcgcgaaa tcaaggcaat caaacgaact    840
tttgattcag ttttaacaat ttatgaaatt atttgagctt atccttttcaa tttcctttttt    900 ctgtttgcta aaattaagga aatgtgattt gcaatatgaa gttttcattt gatagagatg     960
```

-continued

```
ttactcaatt tctaaattga tgtgtcaatc agatatttga agaaaagctt tgcatgggtc    1020
tatccatgcc ggtaaacgaa tctattaaaa attgttcccc tttgggacca acaaaagaa     1080 atttgtaaat aataaaaaac actaccaaac catattaata tggataagga tttccttttc    1140
atgtatatat ttagacatct aaaaatgaag gattccaatt ttttgttata ggataaggtg    1200
atcgatcgat ttttttcctt ttatttgtct taaatcatcc aatccgattt ctgtttttct    1260
tattttattt tcatttaatc atcattcacc caatatcttt tcttagctaa taagttgtgt    1320
gtttgatgat tatactttaa cgtgatgtgt tctgtttcta gcatgggttg ctattttttc    1380
tctctcaaag ttttttttat gtggattact taggacgagg ttttcaagg ccacttctta    1440 tccatgctct ctgtattagt tcatttcgtt aattatgaac gaaatccttt atcaccttaa    1500 aaaaaaagt gtgtttcatg cgggaacttt aatgaaaagt tcccggtact gttcacttaa    1560
cgaaaaatca cattttttaca ctaaaaagtc aatccttgta ctattcactt tacccttttat  1620 tttgtcttta tcgttaaaac tcaaagtttt caaatcattt tcattagttt tccttatata    1680
taattatgtg tttatacttt tcaggtaatg aaacgatata cacaagatcc tatacaacca    1740
ataacatacg agaatttatc aagaatcgaa aaacaataaa taggtttgtt ggttttcatg    1800
actttaagct tgattttcca tttacccctta cggaaaagtc taaattgata tgtgtacaaa    1860
agtcacaaga caatagtaaa attaagcttc agggaaaata caagaatcac cttacttgga    1920
cggtgctcaa tactattcat tctttaaaga ttaaaataaa ttactttact tttggtcata    1980
cttgtcggaa agtatcaaga tcaagttgcc acatatttaa tgtacggctt gcaagcagtg    2040
atgcagttat acttttgact ccagaacaaa gaatttccag tgccctctct ggacattgaa    2100
gctagctacc gatcgtggtc cgacacgtgt gcaatcgatg ttgcatggaa attttgtttt    2160
cttctcattt tttctccatt taaccatcaa ggttcaaact attatcgtta tgctaggtga    2220
tgaagcttgt gagtgactaa caaatacatc aatccccaaa tcttatgaga caaactcaac    2280
aatgtttgtt ggtctaattt gaatattgaa tatttaaaat tgttttatat atcaagaaat    2340
aattgatgtt tctattactt acattaatca tgaaattacc aaaatttagc ccatgagggt    2400
tggcttagta ggtaagatct ttactttgtg tgccgtcccc ccaaggtttg agtcctgttg    2460
tcagtagtca ttttttatgt gatatgtaaa ttcctacgta aatccatact gatggtagct    2520
gacagttagg tgtcatgcgt aagtccttcc ggctcaaagt tgtggacatg tcttggcact    2580
gatatagtga gaataatcaa tctcccccta agttttgtta ccgaaaaaaa aaaccaaat    2640 tttagtatta attgttgtaa taatttagct cccccctggat tcttacagtg ccatttgaag    2700
aaagactttg tcgaaagaaa ttgccctgat atcatttatg tggtaaaaaa cagcctaggt    2760
tccaaaataa agatattatt cttaaaatga ctttttccata tcagttgtct atgcatgc     2818
```

<210> SEQ ID NO 16
<211> LENGTH: 5407
<212> TYPE: DNA
<213> ORGANISM: Malus domestica

<400> SEQUENCE: 16

```
gagctcgtta aataaaatat ttgatttcta aaaaaaatgg acccccctaaa taaagtattt    60 ggattctaga tataatatct ctttcttttt gttattatat tttcaatata attattagtt    120
cggtgataga tattagttat ttggttttca gtgtatggag attagttgtt taatttgtgt    180
ataattattc ttcatttgtt tttgttaaat gtaattttt tttcaaaaa tttatttgta    240 attggtatct ctggatttta ctaactagtt tgtgtgtttt ctttataatg ctaaactgct    300
```

-continued

```
aattgcttga aaactttata gttgcatgca tattctagtt ttgaagtaag gtatgaaact    360
agtattttag atgcaatggg taagttgatg atataaatga gtcatctttt gaaagtcttc    420
ttttaatttt atctgataat agtttgtcac aagactcgtt tggaagtact tttaaaatga    480
ctgaaagcac ttttggtgaa attgattttg gttccaaaag cgtgctttt  ggaagaagca    540
tcaggtattt gcttctatac ttcttgtaga aagcacttta agtgcttttc catgatgcac    600
ttgaattttt attgaagatt ggtttcaaaa acattttcac taaaagcgct tcaaacatt     660
ttaaaaacac ttccaaacga acccataata gaaggaaatt tatagtaccc tttttattaa    720
ttcataaata atctaatgtt aaatcctttg aaagtatata gtgtatataa tttcatggaa    780
tcataattaa cagaagtatt gagatgaata cattgatggg agaatgggcc ttgcatcaaa    840
ctataagttg ggttattccc tatattattg attgatttta tggtggatcc tcaaatttgt    900
catgatatca tagcaagttg acccatgtgt aatagtgaac acaccatgc  aacaatcctc    960
gcaaccagta gtggccctttg tagcgaggca ataaccctttg cagccggtag cagtgtgcgg   1020
cagtcaatgc catggcagtg cagcacgaag aagcagccat aacagtgcaa cacgtagaaa   1080
gcagtgcagc aaggcagcag cggtgcaaca acaagcaatg cagtgtacaa tagtggcaaa   1140
aatgcaactg gcaatgcaaa cattagcgag tgagtcgaca agcaatgcga acattaacgt   1200
gacataagat ggatttcggt catccaaggt tatttaggcc atctccaacc gaaggaagca   1260
agagggcttg ttttagccct ttggcccctcc aagaatataa tattttaatg aatagtgcaa   1320
ggctatattt cttaccatat ccaaccaagg ggccaaagaa ccataggcca aacatagccc    1380
tgtgacaaaa aatcatctcc aaccgaggtc caaagagtca tagggccaaa cataatttat    1440
tattttaatt gaattactat ggttacttaa attaaattac ctcaataatt ttatgttatg    1500
gattgtcaat aattttcatg ttgttaaatg ttttaaaaaa tgttgtttaa atttcatatt    1560
gttaattttt ttttatgttg tttaatgtta cttaatgtta tttaatgttg tttaatattg    1620
tttaatgttg tttcatgtta cttaatgtca cttaatgttg tttaatgact taggaagtta    1680
taggaaaaaa atagaatttt taatttttt  ttaattttgt aaaataaaaa aattaaatat    1740
gatgtcaaca tgtggcttgg cccaaggctg gcttgttggc gaggttgggc caaccagttg    1800
gcccctttggc cctttttttgt ccaatggggc ccacaagcct tttggcctag ccctcggttg    1860
gagacagttt tcggtctatt ttcggccctc tagccctctg gactatttgg ttggagatgg    1920
ctttagaccc caaaaactgc gttttagaaa atttacaaac ttttcatttt tgtccgatcc    1980
actttcatta ccctccctag agcttcccta cattcgcaga gtagttttga gtcattacac   2040
tttataattc accacattcc cgaaggaaga actaagtcta ataaagcttt atggagccaa    2100
ataggtaaag tgtgtgcatc tctgccaaag gaaaatagaa ggcttcaaat cacaagtcta    2160
aaagaagagg agaggcttca aattaaatta caagtccgtc tcatagggtc ctcatatgcc    2220
tattcattca tttcatatta acggtggtag cctaaataag cacgaaagcg ttcactttga    2280
gaggctttaa accataagtt tgtgaaccat gtttcatagc tcacacttgt gttcttcatc    2340
aagttcatgg agaattacca agcacaacaa atacatgtgt tggttcatcc acattaaagt    2400
cgaagattgc ccgccacatg aaactcctgg tggtcccatt cattcaagat caaacctcga    2460
cgacccctaa agaaattata agtctaattc aagaccaaga gtacaccacc cttgaataaa    2520
attcgctcta gaggaatgaa gtaaatccaa acctttggag gaaaccagaa agctctttgc    2580
ccaaagaaaa cattataatt cttcatcaag cttgtggaga ttcaacaagc acaaaaaaaa    2640
```

```
aaaaaaaaaa aaaaaaaaac acataccgat tcgtccacca tcacgtgaaa ctcttcatgg    2700
tcccgtttca ttcaagacaa gcctcgatgg cccttgaaga aactttcagc ccaattatag    2760
atcaagcctc aatggtcttg catcgacatc tatgttgaga gacttcaaag catactgatc    2820
aaaatacatt cactatgtgg agggacttca aaacgcacat tctacacgtg acaagcacat    2880
atatacacca tgccttgaaa tggggtcatt cgtagacatc aaaattttag tgaagtaaat    2940
gtttaccaac acaataaaat cttgacgtgc tagggcttac ttggcatgca ccatgtgtct    3000
cacaaatcgt acaaatagca tgtagcttat caaaactaga cgagtcatca agagtgacac    3060
gtgtcaacat ttggcaaaaa ttaattaagg atttatcctt attaattctt tgattaattt    3120
aacttaaatc aaataaatta attgatttaa atttaaaatg tgattgatta attgatggag    3180
tcaaatcacg aaccaagctt caaatcaagt tctggttctt tcatcgatga ataaaatcca    3240
caatcaaggc caaatccaac tgtaggcaag actaggagag cctataaata cgaggctcca    3300
agacaaagaa atgggtcaga aattcatcaa aacacctaga ctctcaaact cccaaacact    3360
cagaagatac agaaaaatct ctgcattctt tgtcatactt gtgaagaacc accaagcacc    3420
tttacacatg ccggttcctc catcgccatt agccaaaacc ctgaggcatt tgtttattcg    3480
agatcaagtc atcacgattt tcggatcaac aacacacact ttttttcacc cagaagatcg    3540
aatcagagga ttaaaaattg tagcagagat tgtaaccta aattcattaa taccaattat    3600
tactttgtat acgtattctt gggttattta ttgcaagaat ttcgtgttta caactcttt    3660
tctagcactt ccatcgactt ataagtaatt taggctattc ttatattacc aattaatttt    3720
tagtggaatc tcaactttt taaaattatt tatctcatgg aaaatccaaa ttctcctcta    3780
aatgaacggt taacaaaaag gaaactttaa cgcaaaactc tcggtactgt tcactttaat    3840
gaaaatcat atttttacat taaaaagtca atcttgttac tattcacttt accctttatt    3900
ttatccttat cgttaaaatt caaagttttc aaacccttt cattagtttt ccttaacaaa    3960
aatggtttta ttataacaaa tgattctagt gttttccttg ttttgtatac ctaattctaa    4020
aggggataga gtgatgatgt taaatgaaga aaaaagaga gatgccattt tgttcgtac    4080
cggattttcg aggttgactc aaatcaaaac attgtttggt aattggagta atgaactgag    4140
cagacataaa aacctgtgcg aacttaaagg ttaaaaaaaa ggttaaaaaa aaaaaactta    4200
aacgaaaaaa tctcagtatt gtttatttta acaaaaaatc acacttttac attaaaaagt    4260
caatcctgtt attatttatt ttacccttta ttttgtttaa aactcaaagt ttttaagtat    4320
ttttcattaa ttttccttaa aaaaaataga aagtgagaaa aatgcccgac aaaattagtt    4380
gtggctacta gagtcaagaa gcatatggac cagggtgggt cgctcttggc atttctatg    4440
atacttgttg tcggtaaggt tttgtaaaca aaactagacc cgagtattaa ttcttgtttc    4500
tttgttttt tttcaattac aagccgatta atgcttctat gtacacttat aatccccacg    4560
caagtttgta ggttatgcca ggtaatggtg aacgccctac ccacttccca gtccaagcaa    4620
atagtgagaa aataaattaa tggatgatac taggaaaatt aaatttggag ataaaatttg    4680
caaattatat aatatgtcac ctatacgaat taacacattt atcaatattt aataataaa    4740
tcaatcatca actaccatat aatttagttt ccaaatttt atttacaaat ttagtctta    4800
gtattcccct caattaatta tttaatgttg attagtaaac actaaaactt cattgctttg    4860
ggatttggga gtgtctgaag gtccttcatg atcaatgtct ttagatggtg gagcaaaagc    4920
gcgtacaatt aattatcatg ttgttttggg attttattg aatcaaaata cttggatcat    4980
aatgttaaga aaagaacca gagaaatcta aagagacttt cttaaaaatg agattcttca    5040
```

```
taatttattt atcatgtttt tggtacaata tttataatat cggggcaaaa attaatgtta    5100
aaatgtaaga taacagagaa ttcatagaaa gcacaatttt aagataatct ccttaacatt    5160
tataaaaaat atgactactc agtgtgacgt gtcattcctt tgttagacaa ataatttcta    5220
tatatttaaa tttatattat tacttttttg ctatatatag acccctccag tccaacaaca    5280
tccaatatcc cacttcaaac ttgtaatcca aaaccaaaac ctcaaactct ctctctattg    5340
ctttctcttc ctttccacac ttctttctta cagcttgtat ccatacacaa gaaaattaac    5400
caaaatg                                                              5407

<210> SEQ ID NO 17
<211> LENGTH: 5407
<212> TYPE: DNA
<213> ORGANISM: Malus domestica

<400> SEQUENCE: 17
cattttggtt aattttcttg tgtatggata caagctgtaa gaaagaagtg tggaaaggaa      60
gagaaagcaa tagagagaga gtttgaggtt ttggttttgg attacaagtt tgaagtggga     120
tattggatgt tgttggactg gagggggtcta tatatagcaa aaaagtaata atataaattt     180
aaatatatag aaattatttg tctaacaaag gaatgacacg tcacactgag tagtcatatt     240
ttttataaat gttaaggaga ttatcttaaa attgtgcttt ctatgaattc tctgttatct     300 tacatttttaa cattaatttt tgccccgata ttataaatat tgtaccaaaa acatgataaa     360
taaattatga agaatctcat ttttaagaaa gtctctttag atttctctgg ttcttttttct    420 taacattatg atccaagtat tttgattcaa taaaaatcca aaacaacat gataattaat      480 tgtacgcgct tttgctccac catctaaaga cattgatcat gaaggacctt cagacactcc     540
caaatcccaa agcaatgaag ttttagtgtt tactaatcaa cattaaataa ttaattgagg     600
gtaatactaa agactaaatt tgtaaataaa attttggaaa ctaaattata tggtagttga     660
tgattgattt attatttaaa tattgataaa tgtgttaatt cgtataggtg acatattata     720
taatttgcaa atttttatctc caaatttaat tttcctagta tcatccatta atttatttc     780 tcactatttg cttggactgg gaagtgggta gggcgttcac cattacctgg cataacctac     840
aaacttgcgt ggggattata agtgtacata gaagcattaa tcggcttgta attgaaaaaa     900
aaacaaagaa acaagaatta atactcgggt ctagttttgt ttacaaaacc ttaccgacaa     960
caagtatcat agaaaatgcc aagagcgacc caccctggtc catatgcttc ttgactctag    1020
tagccacaac taattttgtc gggcattttt ctcactttct attttttta aggaaaatta     1080 atgaaaaata cttaaaaact ttgagtttta acaaaataa agggtaaaat aataataac      1140 aggattgact ttttaatgta aaagtgtgat ttttttgttaa ataaacaat actgagattt    1200 tttcgtttaa gttttttttt tttaaccttt tttttaacct ttaagttcgc acaggttttt    1260
atgtctgctc agttcattac tccaattacc aaacaatgtt ttgatttgag tcaacctcga    1320
aaatccggta cgaacaaaaa tggcatctct ctttttttct tcatttaaca tcatcactct    1380 atcccctttta gaattaggta tacaaaacaa ggaaaacact agaatcattt gttataataa    1440
aaccattttt gttaaggaaa actaatgaaa agggtttgaa aactttgaat tttaacgata    1500
aggataaaat aaagggtaaa gtgaatagta acaagattga cttttaatg taaaaatatg      1560 attttttcatt aaagtgaaca gtaccgagag ttttgcgtta agtttccttt tttgttaacc    1620
gttcatttag aggagaattt ggattttcca tgagataaat aattttaaaa aagttgagat    1680
```

-continued

```
tccactaaaa attaattggt aatataagaa tagcctaaat tacttataag tcgatggaag    1740
tgctagaaaa agagttgtaa acacgaaatt cttgcaataa ataacccaag aatacgtata    1800
caaagtaata attggtatta atgaatttag ggttacaatc tctgctacaa tttttaatcc    1860
tctgattcga tcttctgggt gaaaaaagt gtgtgttgtt gatccgaaaa tcgtgatgac     1920
ttgatctcga ataaacaaat gcctcagggt tttggctaat ggcgatggag gaaccggcat    1980
gtgtaaaggt gcttggtggt tcttcacaag tatgacaaag aatgcagaga ttttctgta     2040
tcttctgagt gtttgggagt ttgagagtct aggtgttttg atgaatttct gacccatttc    2100
tttgtcttgg agcctcgtat ttataggctc tcctagtctt gcctacagtt ggatttggcc    2160
ttgattgtgg atttattca tcgatgaaag aaccagaact tgatttgaag cttggttcgt     2220
gatttgactc catcaattaa tcaatcacat tttaaattta aatcaattaa tttatttgat    2280
ttaagttaaa ttaatcaaag aattaataag gataaatcct taattaattt ttgccaaatg    2340
ttgacacgtg tcactcttga tgactcgtct agttttgata agctacatgc tatttgtacg    2400
atttgtgaga cacatggtgc atgccaagta agccctagca cgtcaagatt ttattgtgtt    2460
ggtaaacatt tacttcacta aaattttgat gtctacgaat gaccccattt caaggcatgg    2520
tgtatatatg tgcttgtcac gtgtagaatg tgcgttttga agtccctcca catagtgaat    2580
gtattttgat cagtatgctt tgaagtctct caacatagat gtcgatgcaa gaccattgag    2640
gcttgatcta taattgggct gaaagttttct tcaaggcca tcgaggcttg tcttgaatga    2700
aacgggacca tgaagagttt cacgtgatgg tggacgaatc ggtatgtgtt ttttttttt    2760
ttttttttt tttttgtgct tgttgaatct ccacaagctt gatgaagaat tataatgttt    2820
tctttgggca aagagctttc tggtttcctc caaaggtttg gatttacttc attcctctag    2880
agcgaatttt attcaagggt ggtgtactct tggtcttgaa ttagacttat aatttcttta    2940
ggggtcgtcg aggtttgatc ttgaatgaat gggaccacca ggagtttcat gtggcgggca    3000
atcttcgact ttaatgtgga tgaaccaaca catgtatttg ttgtgcttgg taattctcca    3060
tgaacttgat gaagaacaca agtgtgagct atgaaacatg gttcacaaac ttatggttta    3120
aagcctctca aagtgaacgc tttcgtgctt atttaggcta ccaccgttaa tatgaaatga    3180
atgaataggc atatgaggac cctatgagac ggacttgtaa tttaatttga agcctctcct    3240
cttctttttag acttgtgatt tgaagccttc tattttcctt tggcagagat gcacacactt    3300
tacctatttg gctccataaa gctttattag acttagttct tccttcggga atgtggtgaa    3360
ttataaagtg taatgactca aaactactct gcgaatgtag ggaagctcta gggagggtaa    3420
tgaaagtgga tcggacaaaa atgaaagtt tgtaaatttt ctaaaacgca gttttggg     3480
tctaaagcca tctccaacca aatagtccag agggctagag ggccgaaaat agaccgaaaa    3540
ctgtctccaa ccgagggcta ggccaaaagg cttgtgggcc ccattggaca aaaagggcc     3600
aagggccaa ctggttggcc caacctcgcc aacaagccag ccttgggcca agccacatgt    3660
tgacatcata tttaattttt ttattttaca aaattaaaaa aaaattaaaa attctatttt    3720
tttcctataa cttcctaagt cattaaacaa cattaagtga cattaagtaa catgaaacaa    3780
cattaaacaa tattaaacaa cattaaataa cattaagtaa cattaaacaa cataaaaaaa    3840
aattaacaat atgaaattta acaacatttt tttaaaacat ttaacaacat gaaaattatt    3900
gacaatccat aacataaaat tattgaggta atttaattta agtaaccata gtaattcaat    3960
taaaataata aattatgttt ggccctatga ctctttggac ctcggttgga gatgattttt    4020
tgtcacaggg ctatgtttgg cctatggttc tttggcccct tggttggata tggtaagaaa    4080
```

```
tatagccttg cactattcat taaaatatta tattcttgga gggccaaagg gctaaaacaa    4140
gccctcttgc ttccttcggt tggagatggc ctaaataacc ttggatgacc gaaatccatc    4200
ttatgtcacg ttaatgttcg cattgcttgt cgactcactc gctaatgttt gcattgccag    4260
ttgcattttt gccactattg tacactgcat tgcttgttgt tgcaccgctg ctgccttgct    4320
gcactgcttt ctacgtgttg cactgttatg gctgcttctt cgtgctgcac tgccatggca    4380
ttgactgccg cacactgcta ccggctgcaa gggttattgc ctcgctacaa gggccactac    4440
tggttgcgag gattgttgca tggtgttgtt cactattaca catgggtcaa cttgctatga    4500
tatcatgaca aatttgagga tccaccataa aatcaatcaa taatataggg aataacccaa    4560
cttatagttt gatgcaaggc ccattctccc atcaatgtat tcatctcaat acttctgtta    4620
attatgattc catgaaatta tatacactat atactttcaa aggatttaac attagattat    4680
ttatgaatta ataaaaaagg tactataaat ttccttctat tatgggttcg tttggaagtg    4740
tttttaaaat gtttgaaagc gcttttagtg aaaatgtttt tgaaaccaat cttcaataaa    4800
aattcaagtg catcatggaa aagcacttaa agtgctttct acaagaagta tagaagcaaa    4860
tacctgatgc ttcttccaaa aagcacgctt ttggaaccaa aatcaatttc accaaaagtg    4920
ctttcagtca ttttaaaagt acttccaaac gagtcttgtg acaaactatt atcagataaa    4980
ttaaaaagaa gactttcaaa agatgactca tttatatcat caacttaccc attgcatcta    5040
aaatactagt ttcataccttt acttcaaaac tagaatatgc atgcaactat aaagttttca    5100
agcaattagc agtttagcat tataaagaaa acacacaaac tagttagtaa aatccagaga    5160
taccaattac aaataaattt ttgaaaaaaa aaattacatt taacaaaaac aaatgaagaa    5220
taattataca caaattaaac aactaatctc catacactga aaaccaaata actaatatct    5280
atcaccgaac taataattat attgaaaata taataacaaa aagaaagaga tattatatct    5340
agaatccaaa tactttattt aggggggtcca ttttttttag aaatcaaata ttttattaa    5400 cgagctc                                                              5407
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
tttcccgggt atggatacaa gctg                                             24

<210> SEQ ID NO 19
<211> LENGTH: 66
<212> TYPE: PRT
<213> ORGANISM: Malus domestica

<400> SEQUENCE: 19

Ala Ala Ser Ala Ser Val Ser Tyr Asp His Lys Ala Ile Ile Ile Asn
 1               5                  10                  15

Gly Gln Lys Arg Ile Leu Ile Ser Gly Ser Ile His Tyr Pro Arg Ser
                20                  25                  30

Thr Pro Glu Met Trp Pro Asp Leu Ile Gln Lys Ala Lys Asp Gly Gly
            35                  40                  45

Leu Asp Val Ile Gln Thr Tyr Val Phe Trp Asn Gly His Glu Pro Ser
        50                  55                  60

```
Pro Gly
 65

<210> SEQ ID NO 20
<211> LENGTH: 55
<212> TYPE: PRT
<213> ORGANISM: Malus domestica

<400> SEQUENCE: 20

Met Arg Met Leu Ser Arg Asn Ala Thr Phe Asn Ser His Gly Gln Asp
  1               5                  10                  15

Ser Ser Tyr Phe Leu Gly Trp Gln Glu Tyr Glu Lys Asn Pro Tyr His
             20                  25                  30

Glu Val His Asn Thr Asn Gly Ile Ile Gln Met Gly Leu Ala Glu Asn
         35                  40                  45

Gln Leu Cys Phe Asp Leu Leu
     50                  55
```